US012797457B2

(12) United States Patent
Stull et al.

(10) Patent No.: US 12,797,457 B2
(45) Date of Patent: Nov. 17, 2026

(54) VACCINE POLYPEPTIDE COMPOSITIONS AND METHODS

(71) Applicants: Arizona Board of Regents on Behalf of the University of Arizona, Tucson, AZ (US); Phoenix Children's Hospital, Inc., Phoenix, AZ (US)

(72) Inventors: Terrence Stull, Phoenix, AZ (US); Daniel Morton, Tucson, AZ (US); Paul Whitby, Phoenix, AZ (US)

(73) Assignees: Arizona Board of Regents on Behalf of the University of Arizona, Tucson, AZ (US); Phoenix Children's Hospital, Inc.

( * ) Notice: Subject to any disclaimer, the term of this patent is extended or adjusted under 35 U.S.C. 154(b) by 1109 days.

(21) Appl. No.: 17/279,277

(22) PCT Filed: Oct. 15, 2019

(86) PCT No.: PCT/US2019/056298

§ 371 (c)(1),
(2) Date: Mar. 24, 2021

(87) PCT Pub. No.: WO2020/081548

PCT Pub. Date: Apr. 23, 2020

(65) Prior Publication Data

US 2022/0047690 A1 Feb. 17, 2022

Related U.S. Application Data

(60) Provisional application No. 62/745,878, filed on Oct. 15, 2018.

(51) Int. Cl.
*A61K 39/02* (2006.01)
*G16B 25/10* (2019.01)

(52) U.S. Cl.
CPC ............ *A61K 39/099* (2013.01); *G16B 25/10* (2019.02)

(58) Field of Classification Search
CPC ................ A61K 39/099; A61K 39/102; A61K 2039/10; A61K 2039/54; A61K 2039/543; A61K 2039/55505; A61K 2039/575; A61K 39/02; A61K 39/00; A61K 38/00; A61K 38/164; A61K 2039/53; A61K 39/0018; G16B 25/10; G16B 40/00; G16B 15/00; G16B 15/20; G16B 15/30; G16B 10/00; G16B 30/10; G16B 20/00; G16B 30/00; G16B 20/30; G16B 35/00; G16B 45/00; A61P 37/04; A61P 31/04; A61P 31/00; C07K 14/235; C07K 14/285; C07K 2319/00; C07K 2319/21; C12N 15/70; C12N 2330/30; C12N 2330/50; C12Q 1/689; G01N 33/56911
See application file for complete search history.

(56) References Cited

U.S. PATENT DOCUMENTS

| | | | |
|---|---|---|---|
| 5,057,540 | A | 10/1991 | Kensil |
| 5,773,600 | A | 6/1998 | Burnette |
| 5,798,103 | A | 8/1998 | Mooi |
| 6,083,743 | A | 7/2000 | Chong |
| 7,402,572 | B2 | 7/2008 | Krieg |
| 8,697,085 | B2 | 4/2014 | Dale |
| 8,895,514 | B2 | 11/2014 | Weinschenk |
| 2005/0249746 | A1 | 11/2005 | Green |
| 2013/0072881 | A1 | 3/2013 | Khandke |
| 2013/0209501 | A1 | 8/2013 | Sellman |
| 2013/0337006 | A1 | 12/2013 | Garcon |

FOREIGN PATENT DOCUMENTS

| | | | |
|---|---|---|---|
| CN | 107312075 | A | 11/2017 |
| GB | 2220211 | A | 1/1990 |

OTHER PUBLICATIONS

Guiso, Nicole, et al. "Intranasal murine model of Bordetella pertussis infection. I. Prediction of protection in human infants by acellular vaccines." Vaccine 17.19 (1999): 2366-2376.*
Wieser A, Romann E, Magistro G, Hoffmann C, Norenberg D, Weinert K, Schubert S2010.A Multiepitope Subunit Vaccine Conveys Protection against Extraintestinal Pathogenic *Escherichia coli* in Mice. Infect Immun78: (Year: 2010).*
Wong, Ting, et al. "Development of RNAseq methodologies to profile the in vivo transcriptome of Bordetella pertussis during murine lung infection." bioRxiv (2017): 140632. (Year: 2017).*
Premjeet, Sandhu, et al. "Enzyme-Linked Immuno-Sorbent Assay (ELISA), basics and it's application: A comprehensive review." J. Pharm. Res 4.12 (2011): 4581-4583. (Year: 2011).*
Pollard, A. J. et al. A guide to vaccinology: from basic principles to new developments. Nature Reviews: Immunology, vol. 21, Feb. 2021, p. 83-100. (Year: 2021).*
Hozori, S. et al. An immunoinformatics approach to design a potential multi-epitope subunit vaccine against Bordatella pertussis. Informatics in Medicine, Unlocked, vol. 42 (2023) 101358, 14 pages. (Year: 2023).*
Murphy, Timothy F., "Vaccines for Nontypeable Haemophilus influenzae: the Future is Now", Clinical and Vaccine Immunology, 22(5)459-466 (May 2015).
Zhu, Yong-Zhang et al., "Gene Expression Profiling-Based In Silico Approach to Identify Potential Vaccine Candidates and Drug Targets against B. pertussis and B. parapertussis", OMICS A Journal of Integrative Biology, 12(3):161-169 (Sep. 2008).

(Continued)

*Primary Examiner* — Mary K Zeman
(74) *Attorney, Agent, or Firm* — FULLER IP LAW LLC; Rodney J. Fuller

(57) ABSTRACT

Immunogenic peptides, fusion polypeptides, and carrier molecules which include the immunogenic peptides, and immunogenic compositions which include these immunogenic peptides, fusion heterologous polypeptides, and/or carrier molecules bearing the peptides, and which are able to elicit antibody production against infectious organisms, are disclosed. Also disclosed are methods of making and their use in causing an antibody response against one or more strains of infectious organism, such as *B. pertussis* (Bp).

4 Claims, 16 Drawing Sheets

Specification includes a Sequence Listing.

(56) References Cited

OTHER PUBLICATIONS

Wieser, Andreas et al., "First multi-epitope subunit vaccine against extraintestinal pathogenic *Escherichia coli* delivered by a bacterial type-3 secretion system (T3SS)", International Journal of Medical Microbiology, 302(1):10-18 (Jan. 2012).

Altschul et al., 1996, Local alignment statistics, Doolittle ed., Methods in Enzymology 266, 460-480.

Altschul, S. F., et al. "Basic local alignment search tool." Journal of molecular biology 215.3 (1990): 403-410.

Bart, M.J. et al., Global Population Structure and Evolution of Bordetella pertussis and Their Relationship with Vaccination. mBio. Mar.-Apr. 2014; 5(2): e01074-14.

Burns Dl, et al. Pertussis Resurgence: Perspectives From the Working Group Meeting on Pertussis on the Causes, Possible Paths Forward, and Gaps in Our Knowledge. J Infect Dis 2014; 209:S32-S5.

CDC, Pertussis (Whooping Cough) www.cdc.gov/pertussis/surv-reporting/cases-by-year.html. 2019.

CDC, Pregnancy and Whooping Cough, www.cdc.gov/pertussis/pregnant/mom/get-vaccinated.html. Version accessed Mar. 1, 2018. Available online at https://web.archive.org/web/20180301001528/https://www.cdc.gov/pertussis/pregnant/mom/get-vaccinated.html.

Gabutti, G., et al. "Pertussis: current perspectives on epidemiology and prevention." Human vaccines & Immunotherapeutics 11.1 (2015): 108-117.

Gish, W. et al. "Identification of protein coding regions by database similarity search." Nature genetics 3.3 (1993): 266-272.

International Searching Authority. International Search Report and Written Opinion for application PCT/US2019/056298. Mailed on Jan. 10, 2020. 12 pages.

Karlin, S. et al. "Methods for assessing the statistical significance of molecular sequence features by using general scoring schemes." Proceedings of the National Academy of Sciences 87.6 (1990): 2264-2268.

Karlin, S., et al. (1993). Applications and statistics for multiple high-scoring segments in molecular sequences. Proceedings of the National Academy of Sciences, 90(12), 5873-5877.

Kensil et al. Structural and Immunological Characterization of the Vaccine Adjuvant QS-21. In Vaccine Design: The Subunit and Adjuvant Approach (eds. Powell and Newman, Plenum Press, NY, 1995).

Klinman, D. M. (2006). Adjuvant activity of CpG oligodeoxynucleotides. International reviews of immunology, 25(3-4), 135-154.

Kohler, G. et al. "Continuous cultures of fused cells secreting antibody of predefined specificity." nature 256.5517 (1975): 495-497.

Kohler, G. et al. (1976). Derivation of specific antibody-producing tissue culture and tumor lines by cell fusion. European journal of immunology, 6(7), 511-519.

Myers, E. W., et al. "Optimal alignments in linear space." Bioinformatics 4.1 (1988): 11-17.

Pearson, W. R., et al. (1988). Improved tools for biological sequence comparison. Proceedings of the National Academy of Sciences, 85(8), 2444-2448.

Persing, D. H., et al. "Taking toll: lipid A mimetics as adjuvants and immunomodulators." Trends in microbiology 10.10 (2002): s32-s37.

Plotkin SA. 2014. Pertussis: Pertussis control strategies and the options for improving current vaccines. Expert Rev Vaccines 13: 1071-1072.

Salmon, K., et al. "Global gene expression profiling in *Escherichia coli* K12: the effects of oxygen availability and FNR." Journal of Biological Chemistry 278.32 (2003): 29837-29855.

Schmidtke AJ, et al. Population diversity among Bordetella pertussis isolates, United States, 1935-2009. Emerg Infect Dis . Aug. 2012.

Searle, L. J., et al. "Variation in siderophore biosynthetic gene distribution and production across environmental and faecal populations of *Escherichia coli*." PloS one 10.3 (2015): e0117906.

Whitby, P. W., et al. "Antisera against certain conserved surface-exposed peptides of nontypeable Haemophilus Influenzae are protective." Plos one 10.9 (2015): e0136867.

Wieser, A., et al. "A multiepitope subunit vaccine conveys protection against extraintestinal pathogenic *Escherichia coli* in mice." Infection and immunity 78.8 (2010): 3432-3442.

Torkashvand, et al., "Subcutaneous administration of a fusion protein composed of pertussis toxin and filamentous hemagglutinin from Bordetella pertussis induces mucosal and systemic immune responses," Iranian Journal of Basic Medical Sciences, vol. 21, No. 7, Jul. 2018, all enclosed pages cited.

* cited by examiner

DAY 7 BoPOLY1 VS CONTROL P=0.001

DAY 3 BpPOLY1 VS CONTROL P=0.032

DAY 7 BpPOLY1 VS CONTROL P=0.09

DAY 10 BpPOLY1 VS CONTROL P=0.0043

DAY 14 BpPOLY1 VS CONTROL P=0.021

DAY 3 BpPOLY3 VS CONTROL P=0.04

DAY 7 BpPOLY3 VS CONTROL P=0.001

PEPTIDES: BP POLY 100 (LOW TRANSCRIPTION)

| ACCESSION# - PEPTIDE#[a] | BP#[b] | GENE NAME/FUNCTION[c] | RELATIVE EXPRESSION[d] |
|---|---|---|---|
| 880852-1 | BP2204 | ompV | 33 |
| 880129-1 | BP1382 | Flagellin unit | 29 |
| 880478-1 | BP1767 | Autotransportor | 137 |
| 880662-3 | BP1989 | Export ptn | 90 |
| 879378-1 | BP0529 | Autotransportor | 265 |
| 881581-1 | BP3006 | pagP | 153 |
| 880169-1 | BP1427 | Flagellin | 35 |
| 880868-4 | BP2224 | bapA | 374 |
| 880439-1 | BP1724 | Con Hyp | 58 |

PEPTIDE SEQUENCE:

880852-1, 880129-1, 880478-1, 880662-3, 879378-1, 881581-1, 880169-1, 880868-4, 880439-1, 880852-1

AMINO ACID SEQUENCE:

EWASDDYMRTWYGISASQAARSEAGLRRYSASSGFKS (SEQ ID NO. 1)
LTGIRFYEGDAFNITLQSGQTLLSGTTVYPLQAVPSASDPKRLTVAYTLPSGPGTTIQVEMND SEVTGGQ (SEQ ID NO. 2)
LHEFSHDDSVDFGGKSYDAELPGSR (SEQ ID NO. 3)
YSSDILPSSEQVSFGSWRFAMGYPQGEQSGDK (SEQ ID NO. 4)
WEGAIGGTGSLHKKGEGKLVLVKDNHHDGGTTIHAGTLQVSRDANLGSGQSAVTLDGGALAV S (SEQ ID NO. 5)
TGYSWHNRAMYSSDKIRSFNELAWGGG (SEQ ID NO.6)
NSVTSGTLAYIADAGAGNTGTGQYSAVSFDGPRAGNYVGRDFRIEFTRDAVTDELQYSVLSDPPVVPPEQPLP ANMPYSEGSVIDMNGVSIKLSGQPEAGDVFTVETPKSWKMGVQGD (SEQ ID NO. 7)
HEFLDGTRVRVAGVPVSSRMARTWGSV (SEQ ID NO. 8)
YANYSLKYSYTPGDFFSTPDTKGTWY (SEQ. ID NO. 9)
EWASDDYMRTWYGISASQAARSEAGLRRYSASSGFKS (SEQ ID NO. 10)

PROPERTIES

MOL WT= 49.7Kda pI= 5.13

FIG. 5

PEPTIDES: BP POLY 101 (HIGH TRANSCRIPTION)

| ACCESSION# - PEPTIDE#[a] | BP#[b] | GENE NAME/FUNCTION[c] | RELATIVE ABUNDANCE[d] |
|---|---|---|---|
| 879650-3 | BP0840 | ompP | 47,656 |
| 881568-1 | BP2992 | pcp | 31,398 |
| 879744-1 | BP0943 | ompA | 30,266 |
| 879974-1 | BP1201 | tcfA | 29,836 |
| 882258-1 | BP3755 | ompW | 24,133 |
| 881875-1 | BP3342 | pal | 17,497 |
| 881386-1 | BP2786 | Con Hyp | 11,819 |

PEPTIDE SEQUENCE:

879650-3, 881568-1, 879744-1, 879974-1, 882258-1, 881875-1, 881386-1, 879650-3

AMINO ACID SEQUENCE:

GRQTNIASKYFGSIDPFGAGFGQANIGMGMSAMNTVRYDN (SEQ ID NO. 11)
KSSGVGLVAGGALGGVAGNAVGGGTGRTIATVGGVILGALAGNAIENRAGKSSGYEITVRLDN GETRVVAQEADVPISVGQRVQVISGAGPTRVTPY (SEQ ID NO. 12)
STLKPEGRQLLDQVAQQAAGTIDLETIIAVGHTDSIGTEAYNKLSERRAAAVKTYLVSKGIDPNRI YTEGKGELQPIASNKTREGRAQNRRVEIEIVGSSRKN (SEQ ID NO.13)
AFHAQGADYTASNGLRIKDDGTNSMLGR (SEQ ID NO. 14)
NYTTFFDTKTHGALEGSDLRLGDSWGLAG (SEQ ID NO. 15)
RSVYFDFDSYTVSEQYRGLVETHARYLASNNQQRIKIEGNTDERGGAEYNLALGQRRADAVRR MMTLLGVSDNQIETISFGKEKPKATGSSEADFAENRRADIVYQR (SEQ ID NO.16)
VASWPVQRPADITASLLQQAAGLAEVVRDPLAFLDEPEAGAGARPANAPEVLLVGTGRRQHLL GPEQVRPLLAMGVGVEAMDTQAAARTYNILMAEGRRVVVALLPDGDS (SEQ ID NO. 17)
GRQTNIASKYFGSIDPFGAGFGQANIGMGMSAMNTVRYDN (SEQ ID NO. 18)

PROPERTIES

MOL WT= 58,700 Da pI= 7.96

FIG. 6

SEQUENCE LISTING

```
<160> NUMBER OF SEQ ID NOS: 19

<210> SEQ ID NO 1
<211> LENGTH: 37
<212> TYPE: PRT
<213> ORGANISM: Bordetella pertussis

<400> SEQUENCE: 1

Glu Trp Ala Ser Asp Asp Tyr Met Arg Thr Trp Tyr Gly Ile Ser Ala
1               5                   10                  15

Ser Gln Ala Ala Arg Ser Glu Ala Gly Leu Arg Arg Tyr Ser Ala Ser
            20                  25                  30

Ser Gly Phe Lys Ser
        35


<210> SEQ ID NO 2
<211> LENGTH: 71
<212> TYPE: PRT
<213> ORGANISM: Bordetella pertussis

<400> SEQUENCE: 2

Leu Thr Gly Ile Arg Phe Tyr Glu Gln Gly Asp Ala Phe Asn Ile Thr
1               5                   10                  15

Leu Gln Ser Gly Gln Thr Leu Leu Ser Gly Thr Thr Val Tyr Pro Leu
            20                  25                  30

Gln Ala Val Pro Ser Ala Ser Asp Pro Lys Arg Leu Thr Val Ala Tyr
        35                  40                  45

Thr Leu Pro Ser Gly Pro Gly Thr Thr Ile Gln Val Glu Met Asn Asp
    50                  55                  60

Ser Glu Val Thr Gly Gly Gln
65                  70


<210> SEQ ID NO 3
<211> LENGTH: 25
<212> TYPE: PRT
<213> ORGANISM: Bordetella pertussis

<400> SEQUENCE: 3

Leu His Glu Phe Ser His Asp Asp Ser Val Asp Phe Gly Gly Lys Ser
1               5                   10                  15

Tyr Asp Ala Glu Leu Pro Gly Ser Arg
            20                  25


<210> SEQ ID NO 4
<211> LENGTH: 32
<212> TYPE: PRT
<213> ORGANISM: Bordetella pertussis

<400> SEQUENCE: 4

Tyr Ser Ser Asp Ile Leu Pro Ser Ser Glu Gln Val Ser Phe Gly Ser
1               5                   10                  15
```

```
Trp Arg Phe Ala Met Gly Tyr Pro Gln Gly Glu Gln Ser Gly Asp Lys
            20                  25                  30


<210> SEQ ID NO 5
<211> LENGTH: 63
<212> TYPE: PRT
<213> ORGANISM: Bordetella pertussis

<400> SEQUENCE: 5

Trp Glu Gly Ala Ile Gly Gly Thr Gly Ser Leu His Lys Lys Gly Glu
1               5                   10                  15

Gly Lys Leu Val Leu Val Lys Asp Asn His His Asp Gly Gly Thr Thr
            20                  25                  30

Ile His Ala Gly Thr Leu Gln Val Ser Arg Asp Ala Asn Leu Gly Ser
        35                  40                  45

Gly Gln Ser Ala Val Thr Leu Asp Gly Gly Ala Leu Ala Val Ser
    50                  55                  60


<210> SEQ ID NO 6
<211> LENGTH: 27
<212> TYPE: PRT
<213> ORGANISM: Bordetella pertussis

<400> SEQUENCE: 6

Thr Gly Tyr Ser Trp His Asn Arg Ala Met Tyr Ser Ser Asp Lys Ile
1               5                   10                  15

Arg Ser Phe Asn Glu Leu Ala Trp Gly Gly Gly
            20                  25


<210> SEQ ID NO 7
<211> LENGTH: 118
<212> TYPE: PRT
<213> ORGANISM: Bordetella pertussis

<400> SEQUENCE: 7

Asn Ser Val Thr Ser Gly Thr Leu Ala Tyr Ile Ala Asp Ala Gly Ala
1               5                   10                  15

Gly Asn Thr Gly Thr Gly Gln Tyr Ser Ala Val Ser Phe Asp Gly Pro
            20                  25                  30

Arg Ala Gly Asn Tyr Val Gly Arg Asp Phe Arg Ile Glu Phe Thr Arg
        35                  40                  45

Asp Ala Val Thr Asp Glu Leu Gln Tyr Ser Val Leu Ser Asp Pro Pro
    50                  55                  60

Val Val Pro Pro Glu Gln Pro Leu Pro Ala Asn Met Pro Tyr Ser Glu
65                  70                  75                  80

Gly Ser Val Ile Asp Met Asn Gly Val Ser Ile Lys Leu Ser Gly Gln
                85                  90                  95

Pro Glu Ala Gly Asp Val Phe Thr Val Glu Thr Pro Lys Ser Trp Lys
            100                 105                 110

Met Gly Val Gln Gly Asp
        115


<210> SEQ ID NO 8
<211> LENGTH: 27
<212> TYPE: PRT
<213> ORGANISM: Bordetella pertussis

<400> SEQUENCE: 8

His Glu Phe Leu Asp Gly Thr Arg Val Arg Val Ala Gly Val Pro Val
```

```
1               5                   10                  15

Ser Ser Arg Met Ala Arg Thr Trp Gly Ser Val
            20                  25


<210> SEQ ID NO 9
<211> LENGTH: 26
<212> TYPE: PRT
<213> ORGANISM: Bordetella pertussis

<400> SEQUENCE: 9

Tyr Ala Asn Tyr Ser Leu Lys Tyr Ser Tyr Thr Pro Gly Asp Phe Phe
1               5                   10                  15

Ser Thr Pro Asp Thr Lys Gly Thr Trp Tyr
            20                  25


<210> SEQ ID NO 10
<211> LENGTH: 37
<212> TYPE: PRT
<213> ORGANISM: Bordetella pertussis

<400> SEQUENCE: 10

Glu Trp Ala Ser Asp Asp Tyr Met Arg Thr Trp Tyr Gly Ile Ser Ala
1               5                   10                  15

Ser Gln Ala Ala Arg Ser Glu Ala Gly Leu Arg Arg Tyr Ser Ala Ser
            20                  25                  30

Ser Gly Phe Lys Ser
        35


<210> SEQ ID NO 11
<211> LENGTH: 40
<212> TYPE: PRT
<213> ORGANISM: Bordetella pertussis

<400> SEQUENCE: 11

Gly Arg Gln Thr Asn Ile Ala Ser Lys Tyr Phe Gly Ser Ile Asp Pro
1               5                   10                  15

Phe Gly Ala Gly Phe Gly Gln Ala Asn Ile Gly Met Gly Met Ser Ala
            20                  25                  30

Met Asn Thr Val Arg Tyr Asp Asn
        35                  40


<210> SEQ ID NO 12
<211> LENGTH: 97
<212> TYPE: PRT
<213> ORGANISM: Bordetella pertussis

<400> SEQUENCE: 12

Lys Ser Ser Gly Val Gly Leu Val Ala Gly Gly Ala Leu Gly Gly Val
1               5                   10                  15

Ala Gly Asn Ala Val Gly Gly Gly Thr Gly Arg Thr Ile Ala Thr Val
            20                  25                  30

Gly Gly Val Ile Leu Gly Ala Leu Ala Gly Asn Ala Ile Glu Asn Arg
        35                  40                  45

Ala Gly Lys Ser Ser Gly Tyr Glu Ile Thr Val Arg Leu Asp Asn Gly
    50                  55                  60

Glu Thr Arg Val Val Ala Gln Glu Ala Asp Val Pro Ile Ser Val Gly
65                  70                  75                  80

Gln Arg Val Gln Val Ile Ser Gly Ala Gly Pro Thr Arg Val Thr Pro
                85                  90                  95
```

Tyr

<210> SEQ ID NO 13
<211> LENGTH: 102
<212> TYPE: PRT
<213> ORGANISM: Bordetella pertussis

<400> SEQUENCE: 13

Ser Thr Leu Lys Pro Glu Gly Arg Gln Leu Leu Asp Gln Val Ala Gln
1 5 10 15

Gln Ala Gly Thr Ile Asp Leu Glu Thr Ile Ile Ala Val Gly His Thr
20 25 30

Asp Ser Ile Gly Thr Glu Ala Tyr Asn Gln Lys Leu Ser Glu Arg Arg
35 40 45

Ala Ala Ala Val Lys Thr Tyr Leu Val Ser Lys Gly Ile Asp Pro Asn
50 55 60

Arg Ile Tyr Thr Glu Gly Lys Gly Glu Leu Gln Pro Ile Ala Ser Asn
65 70 75 80

Lys Thr Arg Glu Gly Arg Ala Gln Asn Arg Arg Val Glu Ile Glu Ile
85 90 95

Val Gly Ser Arg Lys Asn
100

<210> SEQ ID NO 14
<211> LENGTH: 28
<212> TYPE: PRT
<213> ORGANISM: Bordetella pertussis

<400> SEQUENCE: 14

Ala Phe His Ala Gln Gly Ala Asp Tyr Thr Ala Ser Asn Gly Leu Arg
1 5 10 15

Ile Lys Asp Asp Gly Thr Asn Ser Met Leu Gly Arg
20 25

<210> SEQ ID NO 15
<211> LENGTH: 29
<212> TYPE: PRT
<213> ORGANISM: Bordetella pertussis

<400> SEQUENCE: 15

Asn Tyr Thr Thr Phe Phe Asp Thr Lys Thr His Gly Ala Leu Glu Gly
1 5 10 15

Ser Asp Leu Arg Leu Gly Asp Ser Trp Gly Leu Ala Gly
20 25

<210> SEQ ID NO 16
<211> LENGTH: 107
<212> TYPE: PRT
<213> ORGANISM: Bordetella pertussis

<400> SEQUENCE: 16

Arg Ser Val Tyr Phe Asp Phe Asp Ser Tyr Thr Val Ser Glu Gln Tyr
1 5 10 15

Arg Gly Leu Val Glu Thr His Ala Arg Tyr Leu Ala Ser Asn Asn Gln
20 25 30

Gln Arg Ile Lys Ile Glu Gly Asn Thr Asp Glu Arg Gly Gly Ala Glu
35 40 45

Tyr Asn Leu Ala Leu Gly Gln Arg Arg Ala Asp Ala Val Arg Arg Met
50 55 60

```
Met Thr Leu Leu Gly Val Ser Asp Asn Gln Ile Glu Thr Ile Ser Phe
65                  70                  75                  80

Gly Lys Glu Lys Pro Lys Ala Thr Gly Ser Ser Glu Ala Asp Phe Ala
                85                  90                  95

Glu Asn Arg Arg Ala Asp Ile Val Tyr Gln Arg
            100                 105


<210> SEQ ID NO 17
<211> LENGTH: 110
<212> TYPE: PRT
<213> ORGANISM: Bordetella pertussis

<400> SEQUENCE: 17

Val Ala Ser Trp Pro Val Gln Arg Pro Ala Asp Ile Thr Ala Ser Leu
1               5                   10                  15

Leu Gln Gln Ala Ala Gly Leu Ala Glu Val Val Arg Asp Pro Leu Ala
            20                  25                  30

Phe Leu Asp Glu Pro Glu Ala Gly Ala Gly Ala Arg Pro Ala Asn Ala
        35                  40                  45

Pro Glu Val Leu Leu Val Gly Thr Gly Arg Arg Gln His Leu Leu Gly
    50                  55                  60

Pro Glu Gln Val Arg Pro Leu Leu Ala Met Gly Val Gly Val Glu Ala
65                  70                  75                  80

Met Asp Thr Gln Ala Ala Ala Arg Thr Tyr Asn Ile Leu Met Ala Glu
                85                  90                  95

Gly Arg Arg Val Val Val Ala Leu Leu Pro Asp Gly Asp Ser
            100                 105                 110


<210> SEQ ID NO 18
<211> LENGTH: 40
<212> TYPE: PRT
<213> ORGANISM: Bordetella pertussis

<400> SEQUENCE: 18

Gly Arg Gln Thr Asn Ile Ala Ser Lys Tyr Phe Gly Ser Ile Asp Pro
1               5                   10                  15

Phe Gly Ala Gly Phe Gly Gln Ala Asn Ile Gly Met Gly Met Ser Ala
            20                  25                  30

Met Asn Thr Val Arg Tyr Asp Asn
        35                  40


<210> SEQ ID NO 19
<211> LENGTH: 249
<212> TYPE: PRT
<213> ORGANISM: artificial sequence
<220> FEATURE:
<223> OTHER INFORMATION: Composition of Bacterial Vaccine Polypeptide
      Hi Poly 1 designed as a linear sequence of H. influenzae peptide
      with BamA-3 at each terminus with Hist-Tag at the N-terminus.

<400> SEQUENCE: 19

Gly Phe Gly Asn Lys Arg Leu Pro Phe Tyr Gln Thr Tyr Thr Ala Gly
1               5                   10                  15

Gly Ile Gly Ser Leu Arg Gly Phe Ala Tyr Gly Ser Ile Gly Pro Asn
            20                  25                  30

Ala Ile Tyr Glu Val Ile Trp Asn Asp Met Arg Glu Gln Val Ala Arg
        35                  40                  45

Gln Leu Ile Val Lys Ile Ile Ala Leu Gln Asn Gln Ile Lys Thr Met
    50                  55                  60
```

-continued

```
Leu Asp Asn Ser Pro Tyr Ala Gly Trp Gln Val Gln Asn Asn Lys Pro
65                  70                  75                  80

Phe Asp Gly Lys Asp Trp Thr Arg Trp Thr Gly Ser Ala Met Pro Gly
                85                  90                  95

Gly Ser Ala Asn Arg Ile Pro Asn Lys Ala Gly Ser Asn Pro Glu Gly
            100                 105                 110

Ser Ile Ala Pro Ile Leu Arg Ile Asn Lys Gln Ile Thr Ser Asp Gln
        115                 120                 125

Val Ala Ser Ile Phe Lys Lys Gly Arg Glu Ala Glu Lys Leu Tyr Asn
    130                 135                 140

Asn Lys Thr Ile Glu Lys Glu Gln Arg Lys Val Asp His Tyr Asp Thr
145                 150                 155                 160

Ser Ser Lys Thr Val Lys Tyr Lys Asp Leu Asn Glu Gln Lys Leu Lys
                165                 170                 175

Pro Gln Glu Ala Gln Thr Asn Leu Val Glu Arg Ala Lys Gly Leu Ser
            180                 185                 190

Glu Asp Gly Asp Asn Leu Asp Asp Phe Gly Asn Thr Val Tyr Gly Lys
        195                 200                 205

Leu Asn Ala Asp Arg Arg Gly Phe Gly Asn Lys Arg Leu Pro Phe Tyr
    210                 215                 220

Gln Thr Tyr Thr Ala Gly Gly Ile Gly Ser Leu Arg Gly Phe Ala Tyr
225                 230                 235                 240

Gly Ser Ile Gly Pro Asn Ala Ile Tyr
                245
```

VACCINE POLYPEPTIDE COMPOSITIONS AND METHODS

CROSS REFERENCE TO RELATED APPLICATIONS

This application is a national phase from the International Patent Application no. PCT/US2019/056298 filed on Oct. 15, 2019 and now published as WO 2020/081548, which claims priority to and benefit of U.S. Provisional Application No. 62/745,878, filed Oct. 15, 2018. The disclosure of each of the above-identified patent applications is incorporated herein by reference.

INCORPORATION-BY-REFERENCE OF MATERIAL ELECTRONICALLY FILED

The official copy of the sequence listing is submitted electronically in ASCII (text) file format having the file name "003US-PAT ST25.txt" created on Aug. 12, 2025, and having a size of 12,622 bytes, and is filed concurrently with the specification. The Sequence Listing ASCII (text) is part of the specification and is herein incorporated by reference in its entirety.

INCORPORATION BY REFERENCE STATEMENT

The entire contents of all references cited in this specification are expressly incorporated herein by reference.

BACKGROUND

Non-toxic, broadly cross-reactive immunoprotective antigens have yet to be identified for many diseases. Moreover, diseases for which effective vaccines exist can increase in prevalence over time due to adaptation to the vaccine components by the organism(s) responsible for the disease.

For example, *Bordetella pertussis* is a Gram-negative, aerobic, pathogenic, encapsulated coccobacillus of the genus *Bordetella*. Its virulence factors include pertussis toxin, filamentous homagglutinin, pertactin, fimbria, and tracheal cytotoxin. The complete *B. pertussis* genome of 4,086,186 base pairs was published in 2003. *Bordetella pertussis* is a human-specific bacterial pathogen that is the most common causative agent of whooping cough, i.e., pertussis. Pertussis is characterized by an early catarrhal phase followed by a severe and prolonged cough. The severity of the cough is worst in unimmunized infants who therefore experience the highest rate of hospitalization and mortality (Gabutti et al.).

Killed whole-cell vaccines were used to prevent pertussis throughout most of the 20$^{th}$ century. Whole-cell vaccines were replaced in the 1990's by acellular pertussis vaccines. Acellular pertussis vaccines consist of 3-5 protein components, i.e., pertussis toxin subunit A (PtxA), fimbriae serotype 2 (fim2), fimbriae serotype 3 (fim3), pertactin (Prn), and filamentous hemagglutinin (FHA) (Plotkin, 2014).

Recently, the number of reported cases of pertussis in the U.S. has increased despite high levels of vaccine coverage [Burns]. From 265,269 reported cases in 1934, reported cases of pertussis were reduced to a nadir of 1010 in 1976. However, the number of reported cases recently peaked to 48,277 cases in 2012; 17,972 cases were reported in 2016 (CDC, Pertussis [Whooping Cough]).

Multiple factors have contributed to the increased incidence of pertussis, including heightened awareness, improved diagnostic methods, and waning immunity after implementing acellular pertussis vaccines. Genetic vaccine escape of *B. pertussis* may also have contributed since *B. pertussis* strains isolated in the United States no longer uniformly express pertactin and FHA [Marieke, Schmidtke]. Because of reduced vaccine effectiveness and the resultant reduction in herd immunity, the current recommendations for pertussis immunization include immunization of every pregnant women during every pregnancy to temporarily provide protection to newborns (CDC, Pregnancy and Whooping Cough).

Thus, development of alternative vaccines to prevent diseases, of which, pertussis is but one recent example, is an important public health need.

SUMMARY OF THE INVENTION

Embodiments herein relate to vaccine compositions and treatments for diseases. In some embodiments, methodologies are disclosed to construct bacterial heterologous polypeptide vaccines from extracellular and surface exposed epitopes.

In particular embodiments, a combination of approaches is employed, e.g., reverse vaccinology and in silico protein structure analysis. Reverse vaccinology uses genomic bioinformatics to identify proteins that are present in all (sequenced) strains and that are likely to have extracellular or surface exposed regions. In silico protein structure analysis identifies regions of these proteins that may be accessible to the immune system.

By integrating reverse vaccinology with in silico protein structure analysis, one can identify the subset of regions potentially exposed to the immune system that are amino acid sequence conserved, i.e., useful as targets against all strains in the species. The extracellular/surface exposed sequence-conserved peptides are then used to design a fused polypeptide that is cloned, expressed, and purified.

These and other aspects are further described below. However, the embodiments and examples described herein are not intended to be limiting.

BRIEF DESCRIPTION OF THE DRAWINGS

Several embodiments of the present disclosure are hereby illustrated in the appended drawings. It is to be noted, however, that the appended drawings only illustrate several typical embodiments and are therefore not intended to be considered limiting of the scope of the present disclosure.

FIG. 5 depicts the design of Bp Poly 100. In this case the individual protein and specific peptide are listed together with the relative expression value of that protein from de Gouw et al. The linear sequence of the linked peptides is shown together with the actual peptide sequences incorporated in to the respective Bp Poly. Alternating bolding denotes the division between individual peptides. Additionally, the calculated molecular weight and pI for each Bp Poly is shown. a) NCBI Accession number of the protein in *B. pertussis* strain Tohama. The suffix is our designated peptide number. b) The curated *B. pertussis* (BP) protein name. c) The gene name or function where known. Con. Hyp=conserved hypothetical. d). Relative abundance of mRNA based on the data of de Gouw et al[1]. The relative expression of the gene determined from a transcriptomic analysis. Values range from 0 to 52,549 for the maximally expressed secreted protein, ptxA.

FIG. 6 depicts the design of Bp Poly 101. In this case the individual protein and specific peptide are listed together with the relative expression value of that protein from de Gouw et al. The linear sequence of the linked peptides is shown together with the actual peptide sequences incorporated in to the respective Bp Poly. Alternating bolding denotes the division between individual peptides. Additionally, the calculated molecular weight and pI for each Bp Poly is shown. a) NCBI Accession number of the protein in *B. pertussis* strain Tohama. The suffix is our designated peptide number. b) The curated *B. pertussis* (BP) protein name. c) The gene name or function where known. Con. Hyp=conserved hypothetical. d). Relative abundance of mRNA based on the data of de Gouw et al 1 The relative expression of the gene determined from a transcriptomic analysis. Values range from 0 to 52,549 for the maximally expressed secreted protein, ptxA.

DETAILED DESCRIPTION

Figure 1:
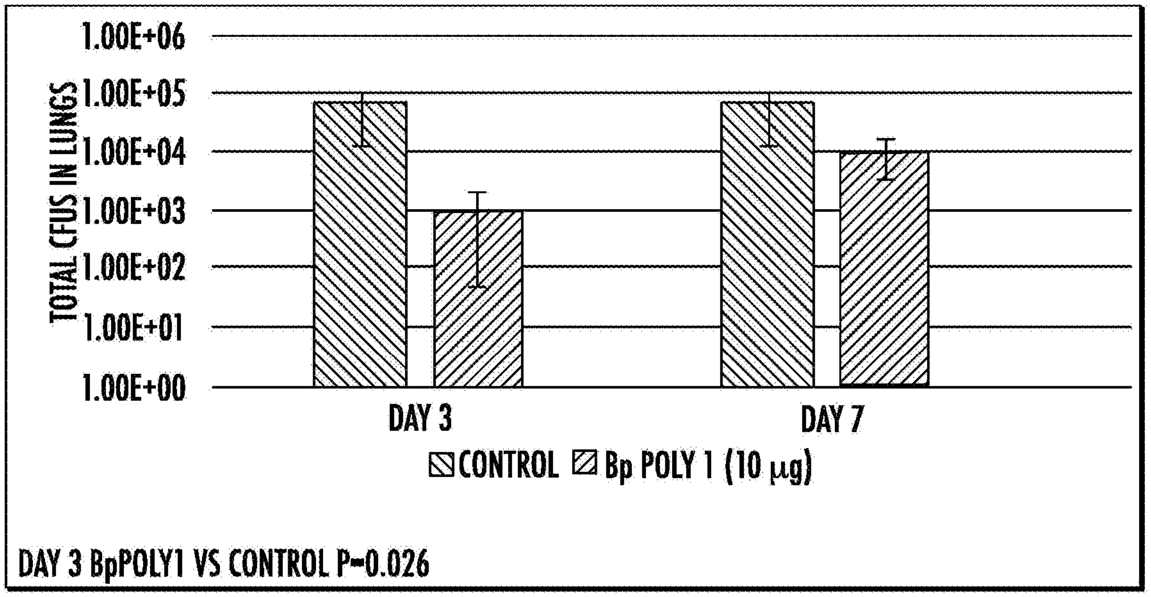
FIG. 1 depicts an experiment in which twelve mice are immunized with BpPoly1; final post-immunization bleed geometric mean titer is 11.22. As illustrated, total colony forming units found in the lungs is less at 3 and 7 days in immunized mice versus control mice.

The present disclosure is directed, in certain embodiments, to immunogenic peptides that are able to elicit antibody production against disease-causing organisms, and, in one example, *Bordetella pertussis* (Bp). The present disclosure is also directed, in certain embodiments, to fusion polypeptides and carrier molecules that include the immunogenic peptides, and to immunogenic compositions that include these immunogenic peptides, fusion polypeptides, and/or carrier molecules bearing the peptides.

The present disclosure is also directed, in certain embodiments, to methods of use of the above immunogenic peptides/polypeptides/carrier molecules/immunogenic compositions in causing an antibody response against one or more strains of a disease causing organism (Bp, for example (but not by way of limitation), as vaccines or for generating antisera for active or passive immunization of subjects.

Before further description of various embodiments of the peptide, fusion polypeptide, and carrier molecule compositions, as well as methods of use thereof, of the present disclosure in more detail, it is to be understood that the present disclosure is not limited in application to the details of methods and compositions as set forth in the following description. The description provided herein is intended for purposes of illustration only and is not intended to be construed in a limiting sense. The present disclosure is capable of other embodiments or of being practiced or carried out in various ways. As such, the language used herein is intended to be given the broadest possible scope and meaning, and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that various embodiments of the present disclosure may be practiced without these specific details.

In other instances, features that are well known to persons of ordinary skill in the art have not been described in detail to avoid unnecessary complication of the description. It is intended that all alternatives, substitutions, modifications, and equivalents apparent to those having ordinary skill in the art are included within the scope of the present disclosure as defined herein. Thus the examples described below, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures, as well as of the principles and conceptual aspects of the present disclosure.

All of the compositions and methods of production and application and use thereof disclosed herein can be made and executed without undue experimentation in light of the present disclosure. Thus, while the compositions and methods of the present disclosure have been described in terms of particular embodiments, it will be apparent to those of ordinary skill in the art that variations may be applied to the compositions and/or methods and in the steps or in the sequence of steps of the methods described herein without departing from the concept, spirit, and scope of the present disclosure.

All patents, published patent applications, and non-patent publications mentioned in the specification are indicative of the level of skill of those skilled in the art to which the present disclosure pertains.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like, is meant to encompass, for example, variations of ±10% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, any reference to "one embodiment" or "an embodiment" means that a particular element, feature, composition, structure, or characteristic described in connection with the embodiment is included in at least one embodiment. The appearances of the phrase "in one embodiment" in various places in the specification are not necessarily all referring to the same embodiment.

The term "mutant" or "variant" is intended to refer to a protein, peptide, or nucleic acid which has at least one amino acid or nucleotide which is different from the wild type version of the protein, peptide, or nucleic acid, and includes, but is not limited to, point substitutions, multiple contiguous or non-contiguous substitutions, chimeras, or fusion proteins, and the nucleic acids which encode them. Examples of conservative amino acid substitutions include, but are not limited to, substitutions made within the same group such as within the group of basic amino acids (such as arginine, lysine, and histidine), acidic amino acids (such as glutamic acid and aspartic acid), polar amino acids (such as glutamine and asparagine), hydrophobic amino acids (such as leucine, isoleucine, and valine), aromatic amino acids (such as phenylalanine, tryptophan, and tyrosine) and small amino acids (such as glycine, alanine, serine, threonine, and methionine). Other examples of possible substitutions are described below.

The term "pharmaceutically acceptable" refers to compounds and compositions that are suitable for administration to humans and/or animals without undue adverse side effects (such as toxicity, irritation, and/or allergic response) commensurate with a reasonable benefit/risk ratio.

By "biologically active" is meant the ability to modify the physiological system of an organism without reference to how the active agent has its physiological effects.

As used herein, "pure" or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm-blooded animal, particularly a mammal. Non-limiting examples of animals within the scope and meaning of this term include dogs, cats, rabbits, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques that are well known in the art.

The term "effective amount" refers to an amount of an active agent that is sufficient to exhibit a detectable therapeutic effect without excessive adverse side effects (such as toxicity, irritation, and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "peptide" is used herein to designate a series of amino acid residues, connected one to the other typically by peptide bonds between the alpha-amino and carbonyl groups of the adjacent amino acids to form an amino acid sequence. The word peptide is not intended to define length but only that it is a portion of a protein. Specifically, surface exposed peptides are any region of a protein exposed to antibody binding. In certain embodiments, the immunogenic peptides can range in length from 8 to 15 to 25 to 40 to 60 to 75 to 100 or more amino acids, for example, 8, 9, 10, 11, 12, 13, 14, 15, 16, 17, 18, 19, 20, 21, 22, 23, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. The term "polypeptide" or "protein" is used herein to designate a series of amino acid residues, connected one to the other typically by peptide bonds between the alpha-amino and carbonyl groups of the adjacent amino acids, wherein the length is longer than a single peptide. A "fusion protein" or "fusion polypeptide" refers to proteins or polypeptides (and may be used interchangeably) which have been created by recombinant or synthetic methods to combine peptides in a serial configuration.

As used herein "immunogenic composition" refers to a composition containing, for example, peptides, polypeptides, fusion proteins, or carrier molecules with peptides or polypeptides conjugated thereto, which elicits an immune response, such as the production of antibodies in a host cell or host organism. The immunogenic composition may optionally contain an adjuvant. In certain embodiments, the immunogenic composition is a vaccine.

Where used herein, the term "antigenic fragment" refers to a fragment of an antigenic peptide described herein that is also able to elicit an immunogenic response.

The term "homologous" or "% identity" as used herein means a nucleic acid (or fragment thereof) or an amino acid sequence (peptide or protein) having a degree of homology to the corresponding reference (e.g., wild type) nucleic acid, peptide, or protein that may be equal to or greater than 70%, or equal to or greater than 80%, or equal to or greater than 85%, or equal to or greater than 86%, or equal to or greater than 87%, or equal to or greater than 88%, or equal to or greater than 89%, or equal to or greater than 90%, or equal to or greater than 91%, or equal to or greater than 92%, or equal to or greater than 93%, or equal to or greater than 94%, or equal to or greater than 95%, or equal to or greater than 96%, or equal to or greater than 97%, or equal to or greater than 98%, or equal to or greater than 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four contiguous amino acids. Also included as substantially homologous is any protein product that may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul (Proc. Natl. Acad. Sci. USA (1990) 87:2264-2268; modified as in Karlin & Altschul (Proc. Natl. Acad. Sci. USA (1993) 90:5873-5877)). In at least one embodiment, "% identity" represents the number of amino acids or nucleotides that are identical at corresponding positions in two sequences of a protein having the same activity or encoding similar proteins. For example, two amino acid sequences each having 100 residues will have 95% identity when 95 of the amino acids at corresponding positions are the same. Similarly, two amino acid sequences each having 100 residues will have at least 90% identity when at least 90 of the amino acids at corresponding positions are the same. Similarly, two amino acid sequences each having 20 residues will have 95% identity when 19 of the amino acids at corresponding positions are the same, or 90% identity when at least 18 of the amino acids at corresponding positions are the same, or 85% identity when at least 17 of the amino acids at corresponding positions are the same, or 80% identity when at least 16 of the amino acids at corresponding positions are the same.

Further, where a sequence is described herein as having "at least X % identity to" a reference sequence, this is intended to include, unless indicated otherwise, all percentages greater than X %, such as for example, (X+1)%, (X+2)%, (X+3)%, (X+4)%, and so on, up to 100%. Another example of a mathematical algorithm used for comparison of sequences is the algorithm of Myers & Miller (CABIOS (1988) 4:11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman (Proc. Natl. Acad. Sci. USA (1988) 85:2444-2448).

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information (Bethesda, MD). These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The terms "polynucleotide sequence" or "nucleic acid," as used herein, include any polynucleotide sequence which encodes a peptide or fusion protein (or polypeptide) including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The polynucleotide sequence encoding a peptide or fusion protein, or encoding a therapeutically effective variant thereof, can be substantially the same as the coding sequence of the endogenous coding sequence as long as it encodes an immunogenically-active peptide or fusion protein. Further, the peptide or fusion protein may be expressed using polynucleotide sequence(s) that differ in codon usage due to the degeneracies of the genetic code or allelic variations. Moreover, the peptides and fusion proteins of the present disclosure and the nucleic acids that encode them include peptide/protein and nucleic acid variants that comprise additional substitutions (conservative or non-conservative).

For example, the immunogenic peptide variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein. Examples of such conservative amino acid substitutions may include, but are not limited to: ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met. One of ordinary skill in the art would readily know how to make, identify, select, or test such variants for immunogenic activity against one or more disease causing organisms.

The terms "infection," "transduction," and "transfection" are used interchangeably herein and refer to introduction of a gene, nucleic acid, or polynucleotide sequence into cells such that the encoded protein product is expressed. The polynucleotides of the present disclosure may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the present disclosure.

In certain embodiments, the present disclosure includes expression vectors capable of expressing one or more fusion polypeptides described herein. Expression vectors for different cell types are well known in the art and can be selected without undue experimentation. Generally, the DNA encoding the fusion polypeptide is inserted into an expression vector, such as (but not limited to) a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Guidance can be found e.g., in Sambrook et al. (Molecular Cloning: A Laboratory Manual, 3d ed., Cold Spring Harbor Laboratory Press, NY 2001)).

The optimum amount of each peptide to be included in the vaccine and the optimum dosing regimen can be determined by one skilled in the art without undue experimentation. For example (but not by way of limitation), the peptide or its variant may be prepared for intravenous (i.v.) injection, sub-cutaneous (s.c.) injection, intradermal (i.d.) injection, intraperitoneal (i.p.) injection, or intra-muscular (i.m.) injection. Particular, non-limiting routes of DNA injection are i.d., i.m., s.c., i.p., and i.v. The peptides may be substantially pure or combined with one or more immune-stimulating adjuvants (as discussed elsewhere herein), or used in combination with immune-stimulatory cytokines, or administered with a suitable delivery system, such as (but not limited to) liposomes. Adjuvants are substances that non-specifically enhance or potentiate the immune response (e.g., immune responses mediated by CTLs and helper-T (TH) cells to an antigen, and would thus be considered useful in the composition of the present disclosure when used as a vaccine. Suitable adjuvants include, but are not limited to: 1018 ISS, aluminium salts such as but not limited to alum (potassium aluminum sulfate), aluminum hydroxide, aluminum phosphate, or aluminum sulfate, Amplivax, AS15, BCG, CP-870,893, CpG7909, CyaA, Mologen's dSLIM, GM-CSF, IC30, IC31, Imiquimod, ImuFact IMP321, interferon-alpha or -beta, IS Patch, ISS, ISCOMs, Juvlmmune, LipoVac, MF59, monophosphoryl lipid A, and other non-toxic LPS derivatives, Montanide IMS 1312, Montanide ISA 206, Montanide ISA 50\1, Montanide ISA-51, OK-432, and OM-174.

Non-limiting examples of other pharmaceutically suitable adjuvants include nontoxic lipid A-related adjuvants such as, by way of non-limiting example, nontoxic monophosphoryllipid A (see, e.g., Persing et al., Trends Microbial. 10:s32-s37 (2002)), for example, 3 De-0-acylated monophosphoryllipid A (MPL) (see, e.g., United Kingdom Patent Application No. GB 2220211). Other useful adjuvants include QS21 and QuilA that comprise a triterpene glycoside or saponin isolated from the bark of the *Quillaja saponaria* Molina tree found in South America (see, e.g., Kensil et al., in Vaccine Design: The Subunit and Adjuvant Approach (eds. Powell and Newman, Plenum Press, NY, 1995); and U.S. Pat. No. 5,057,540). Non-limiting examples of other suitable adjuvants include polymeric or monomeric amino acids such as polyglutamic acid or polylysine, liposomes, and CpG (see, e.g., Klinman (Int. Rev. Immunol. (2006) 25(3-4):135-54), and U.S. Pat. No. 7,402,572). Other examples of adjuvants that may be used in the compositions disclosed herein include but are not limited to those disclosed in U.S. Pat. No. 8,895,514.

Cytotoxic T-cells (CTLs) recognize an antigen in the form of a peptide bound to an MHC molecule (e.g., class I or II) rather than the intact foreign antigen itself. The MHC molecule itself is located at the cell surface of an antigen presenting cell (APC). Thus, an activation of CTLs is only possible if a trimeric complex of peptide antigen, MHC molecule, and APC is present. Correspondingly, certain embodiments of the present disclosure include compositions including APCs having the peptides displayed thereon via MHC molecules.

In other embodiments, the composition may include sugars, sugar alcohols, amino acids such as glycine, arginine, glutamic acid and others as framework former. The sugars may be mono-, di-, or trisaccharides. These sugars may be used alone as well as in combination with sugar alcohols. Non-limiting examples of sugars include: glucose, mannose, galactose, fructose or sorbose as monosaccharides; saccharose, lactose, maltose or trehalose as disaccharides; and raffinose as a trisaccharide. A sugar alcohol may be, for example (but not by way of limitation), mannitol and/or sorbitol. Furthermore, the compositions may include physiological well tolerated excipients such as (but not limited to) antioxidants like ascorbic acid or glutathione; preserving agents such as phenol, m-cresol, methyl- or propylparaben, chlorobutanol, thiomersal (thimerosal), or benzalkoniumchloride; and solubilizers such as polyethylene glycols (PEG), e.g., PEG 3000, 3350, 4000 or 6000, or cyclodextrins, e.g., hydroxypropyl-cyclodextrin, sulfobutylethyl-cyclodextrin or y-cyclodextrin, or dextrans or poloxamers, e.g., poloxamer 407, poloxamer 188, Tween 20 or Tween 80.

In other embodiments, the present disclosure includes a kit comprising (a) a container that contains one or more pharmaceutical compositions as described herein, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (vii) a syringe. The container is (in particular, non-limiting embodiments) a bottle, a vial, a syringe, or a test tube; and it may be a multi-use container. The container may be formed from a variety of materials such as (but not limited to) glass or plastic. The kit and/or container may contain instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous or intramuscular administration. The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution). The kit may further include other materials desirable from a commercial and user standpoint, including other buffers, diluents, filters, needles, syringes, and package inserts with instructions for use.

An antibody that specifically binds to an immunogenic peptide (and to a fusion polypeptide, dimeric peptide, full length or mature protein, or bacteria expressing the protein) may belong to any immunoglobulin class, for example IgG, IgE, IgM, IgD, or IgA. For characterizing the immunogenic peptides and fusion polypeptides described herein, use of polyclonal and/or monoclonal antibodies may be desired. The antibody may be obtained from or derived from an animal, for example, fowl (e.g., chicken) and mammals, which include but are not limited to a mouse, rat, chinchilla, hamster, rabbit, other rodent, a cow, horse, sheep, goat, camel, human, or other primate. As described herein, polyclonal antisera are obtained from an animal by immunizing the animal with an immunogenic composition comprising an immunogenic peptide, a plurality of immunogenic peptides, a fusion polypeptide, or a plurality of fusion polypeptides.

The level to which antibodies bind to an immunogenic peptide or fusion polypeptide as described herein can be readily determined using any one or more immunoassays that are routinely practiced by persons having ordinary skill in the art. By way of non-limiting example, immunoassays include ELISA, immunoblot, radioimmunoassay, immunohistochemistry, and fluorescence activated cell sorting (FACS).

Non-human animals that may be immunized with any one or more of the immunogenic peptides, fusion polypeptides, or immunogenic compositions comprising the same, include by way of non-limiting example: mice, rats, rabbits, hamsters, ferrets, dogs, cats, camels, sheep, cattle, pigs, horses, goats, chickens, llamas, and non-human primates (e.g., cynomolgus macaque, chimpanzee, rhesus monkeys, orangutan, and baboon). Adjuvants typically used for immunization of non-human animals include, but are not limited to, Freund's complete adjuvant, Freund's incomplete adjuvant, montanide ISA, Ribi Adjuvant System (RAS) (GlaxoSmithKline, Hamilton, Mont.), and nitrocellulose-adsorbed antigen. In general, after the first injection, a subject receives one or more booster immunizations according to a particular (but non-limiting) schedule that may vary according to, inter alia, the immunogen, the adjuvant (if any), and/or the particular subject species.

In animal subjects, the immune response may be monitored by periodically bleeding the animal, separating the sera from the collected blood, and analyzing the sera in an immunoassay, such as (but not limited to) an ELISA assay, to determine the specific antibody titer. When an adequate antibody titer is established, the animal subject may be bled periodically to accumulate the polyclonal antisera. Polyclonal antibodies that bind specifically to the immunogen may then be purified from immune antisera, for example, by affinity chromatography using protein A or protein G immobilized on a suitable solid support, as understood by persons having ordinary skill in the art. Affinity chromatography may be performed wherein an antibody specific for an Ig constant region of the particular immunized animal subject is immobilized on a suitable solid support. Affinity chromatography may also incorporate use of one or more immunogenic peptides, or fusion proteins, which may be useful for separating polyclonal antibodies by their binding activity to a particular immunogenic peptide. Monoclonal antibodies that specifically bind to an immunogenic peptide and/or fusion protein, and immortal eukaryotic cell lines (e.g., hybridomas) that produce monoclonal antibodies having the desired binding specificity, may also be prepared, for example, using the technique of Kohler and Milstein ((Nature, 256:495-97 (1976); and Eur. J. Immunol. 6:511-19 (1975)) and improvements thereto.

The immunogenic compositions described herein may be formulated by combining a plurality of immunogenic peptides and/or a plurality of fusion polypeptides and/or carrier molecule-linked immunogenic peptides with at least one pharmaceutically acceptable excipient. As described herein the immunogenic compositions may further comprise a pharmaceutically suitable adjuvant. Typically, all immunogenic peptides or all fusion polypeptides intended to be administered to a subject are combined in a single immunogenic composition, which may include at least one pharmaceutically acceptable excipient and which may further include at least one pharmaceutically suitable adjuvant. Alternatively, for example, multiple immunogenic compositions may be formulated separately for separate administration, which could be by any route described herein or otherwise known in the art and which could be sequential or concurrent.

The immunogenic compositions described herein may be formulated as sterile aqueous or non-aqueous solutions, suspensions, or emulsions, which as described herein may additionally comprise a physiologically acceptable excipient (which may also be called a carrier) and/or a diluent. The immunogenic compositions may be in the form of a solid, liquid, or gas (aerosol). Alternatively, immunogenic compositions described herein may be formulated as a lyophilate (i.e., a lyophilized composition), or may be encapsulated within liposomes using technology well known in the art. As noted elsewhere herein, the immunogenic compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins (such as albumin), polypeptides or amino acids such as glycine, antioxidants, chelating agents such as EDTA or glutathione, stabilizers, dyes, flavoring agents, suspending agents, and/or preservatives. In general, as discussed herein, the type of excipient is selected on the basis of the mode of administration. The compositions and preparations described herein may be formulated for any appropriate manner of administration, including, for example (but not by way of limitation): topical, buccal, lingual, oral, intranasal, intrathecal, rectal, vaginal, intraocular, subconjunctival, transdermal, sublingual, or parenteral administration.

Dosage size may generally be determined in accordance with accepted practices in the art. The dose may depend upon the body mass, weight, or blood volume of the subject being treated. In general, the amount of an immunogenic peptide(s), fusion polypeptide(s), and/or carrier molecule composition(s) as described herein that is present in a dose, is in a range of, for example (but not limited to), about 1 μg to about 100 mg, from about 10 μg to about 50 mg, from about 50 μg to about 10 mg and comprising an appropriate dose for a 5-50 kg subject. Booster immunizations may be administered multiple times (e.g., two times, three times, four times, or more), at desired time intervals ranging from, for example, about 2 weeks to about 26 weeks, such as about 2, 4, 8, 12, 16, or 26 week intervals. The time intervals between different doses (e.g., between the primary dose and second dose, or between the second dose and a third dose) may not be the same, and the time interval between each two doses may be determined independently. Non-limiting embodiments of therapeutically effective amounts of peptides or fusion polypeptides of the present disclosure will generally contain sufficient active substance to deliver from about 0.1 μg/kg to about 100 mg/kg (weight of active substance/body weight of the subject). Particularly, the composition will deliver about 0.5 μg/kg to about 50 mg/kg, and more particularly about 1 μg/kg to about 10 mg/kg.

In certain embodiments, the present disclosure is directed to peptide compositions comprising at least one or two or three or four or five or more (e.g., 6, 7, 8, 9, 10, 11, 12, 13, 14, 15, 16, 17, 18, 19, 20 or more) different peptides having an amino acid sequence as set forth in the group of peptides shown in Table 1, Table 3, or Table 4, and/or a variant amino acid sequence thereof that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% identity to said peptide(s) in a given group or the variant amino acid sequence, and a pharmaceutically acceptable carrier.

The peptides can be either concentrated (conjugated in series with or without linker sequences between the peptides to form one or more fusion polypeptides) or conjugated to one or more carrier molecules, as described in further detail below. For example, the peptides may be conjugated or otherwise coupled to a suitable carrier molecule such as, but not limited to, tetanus toxoid protein, diphtheria toxoid protein, CRM197 protein, *Neisseria meningitidis* outer membrane complex, *Haemophilus influenzae* protein D, pertussis toxin mutant, keyhole limpet haemocyanin (KLH), ovalbumin, and/or bovine serum albumin (BSA). Other examples of carrier proteins that may be used include, but are not limited to, those disclosed in U.S. Published Patent Applications 2013/0072881, 2013/0209503, and 2013/0337006.

In certain embodiments, the one or more immunogenic peptides comprise, or are contained within, a single fusion polypeptide, or are coupled to one or more carrier molecules. Additional peptides may optionally be provided in a separate fusion polypeptide or carrier molecule than the composition containing the first fusion polypeptide. In one particular embodiment, the fusion polypeptide or carrier molecule comprises at least 1, 2, 3, 4, 5, 6, 7, 8, 9, 10, or 11 immunogenic peptides, at least 5 of which are different from each other. The order in which the immunogenic peptides are linked on the fusion polypeptides may be readily determined by a person of ordinary skill in the art using methods and techniques described herein and routinely practiced in the art, and therefore the order does not require undue empirical, trial and error analysis to ensure optimization of the immunogenicity of each fusion polypeptide. In certain embodiments, the immunogenic peptide at the amino-terminal end of the fusion polypeptide is repeated (i.e., duplicated) at the carboxy terminal end of the fusion polypeptide. Methods of formation of such fusion polypeptides (fusion proteins) are known by persons having ordinary skill in the art; thus, it is not considered necessary to include a detailed discussion thereof herein. However, non-limiting exemplary methods for the formation of fusion polypeptides are shown in U.S. Pat. No. 8,697,085, the entirety of which is hereby explicitly incorporated by reference herein.

In still other embodiments, immunogenic polypeptides that are heterologous in nature are disclosed. Heterologous means composed of peptides with sequences derived from the sequences of peptide regions at different loci on the same protein and/or derived from different proteins within the same strain, species or organism.

The embodiments of the present disclosure will be more readily understood by reference to the following examples and description, which as noted above are included merely for purposes of illustration of certain aspects and embodiments of the present disclosure, and are not intended to be limiting. The following detailed examples and methods describe how to make and use various peptides, fusion proteins, and peptide-linked immunogenic carrier molecules of the present disclosure and are to be construed, as noted above, only as illustrative, and not limitations of the disclosure in any way whatsoever. Those skilled in the art will promptly recognize appropriate variations from the materials and procedures described herein.

As described herein, the approach of delivering extracellular/surface exposed, sequence conserved peptides as a fused polypeptide has several advantages over other vaccine approaches. First, the vaccine includes only epitopes that are useful in protection instead of an entire protein consisting of many regions that may not contribute to protection. Second, these vaccines target many proteins while simultaneously using a practical delivery system. For example, the two polypeptides tested as described herein against *B. pertussis*, Bp Poly 1 and Bp Poly 3, target 21 epitopes (from 13 proteins) and 30 epitopes (from 12 proteins), respectively. This may be important for both protection effectiveness (large number of targets) and for preventing the selection of mutants that genetically escape vaccines.

Peptides alone are too small to be reliably immunogenic. In contrast, the polypeptides are immunogenic. This is functionally similar to attaching a peptide to a carrier protein except the fused peptides function as self-carriers. Moreover, manufacturing a linear polypeptide is simple and inexpensive.

EXAMPLES

Example 1: Design of Antigens

Presence and conservation of putative vaccine components across all isolates of a targeted organism is a prerequisite to development of a successful vaccine. Thus, conserved antigenic targets for prevention of a disease, such as *Bordetella pertussis* infection, are sought. Initially, multiple bioinformatic analysis tools may be used to identify the complement of putative surface-exposed proteins (SEPs) of the *B. pertussis* strain Tohama, essentially as previously described for *Haemophilus influenzae* (Whitby et al 2015, PLoS One e0136867). Having identified the SEP complement of the strain Tohama, one can then use the Basic Local Alignment Search Tool (BLAST; available at blast.ncbi.nlm.nih.gov/Blast.cgi) to determine the presence or absence of each SEP in all completely sequenced *B. pertussis* isolates available in public databases. In this manner, all SEPs conserved across all strains of *B. pertussis* were identified.

The identified conserved SEPs of *B. pertussis* were individually examined to determine homology to other known structurally defined proteins using modeling algorithms available through The Protein Model Portal (www.proteinmodelportal.org). Generated structures were compared and visualized using Chimera to identify potentially surface exposed regions.

From the generated protein models, predicted surface-exposed regions greater than 25 amino acids long were selected. Multiple sequence alignments were performed for each core protein. All available *B. pertussis* protein sequences for each individual SEP were used to perform these alignments; alignments were used to confirm sequence conservation of each predicted surface-exposed region. Surface exposed regions with 100% conservation at the amino acid level across the species were selected as potential peptide antigens for further examination.

Subsets of these conserved surface exposed peptides were linked sequentially to generate three individual polypeptides. Linkage was achieved by synthesis of an artificial DNA fragment encoding each of the selected peptides in sequence with the first peptide repeated at the end (Thermo Fisher Scientific). The artificial DNA fragment was inserted in to the expression vector pET100 to allow for inducible expression of the encoded polypeptide and additionally incorporated a polyhistidine-tag to facilitate metal-affinity purification of the expressed polypeptide.

As used herein, the polypeptide "BpPoly1" includes 21 unique peptides from 13 *B. pertussis* proteins and has a theoretical molecular weight of 99-kDa. Also as used herein, the polypeptide "BpPoly3" contains 30 unique peptides derived from 12 proteins and is 99-kDa in molecular weight.

Purification of Polypeptides

Plasmid constructs encoding polypeptides were transformed into *E. coli* BL21 Star(DE3). *E. coli* cultures were grown with shaking to an OD at 600 nm of 0.5-0.7 at which OD they were induced by addition of 1 mM IPTG. Following IPTG addition cultures were incubated with shaking for 4 hrs at which point cells were recovered by centrifugation and frozen for subsequent purification procedures.

Thawed cell pellets were resuspended in CelLyticB (10 ml/gram of cells) containing 200 μg/ml lysozyme and 50 units/ml benzonase and incubated for 1 hr at RT. Following centrifugation at 16,000 g for 15 minutes, the pellet was resuspended in Guanidine lysis buffer with rocking for 1 hr at RT. Following a second identical centrifugation the supernatant was reserved for application to an equilibrated Ni purification column. Following three washes polypeptide bound to the Ni column was eluted by standard protocols and fractions of 1 ml collected. Purity of purified polypeptides was assessed by SDS-PAGE and fractions with purity >90% were selected for downstream use.

Immunization of Mice

Groups of 12 or 24 naïve female BALB/c mice (4-6 weeks old) were immunized intramuscularly on days 0, 14, and 28 with 10 μg of purified polypeptide bound to alum adjuvant (AdjuPhos; Invivogen) and 2 μg of monophosphoryl lipid A (MPLA; Sigma). Control groups were immunized with AdjuPhos and MPLA only. Prior to each immunization and 20 days after the final immunization, mice were bled to obtain sera for determination of antibody titer by ELISA.

Infection of Mice

On day 49, lightly anesthetized mice were challenged intranasally with approximately 3,000 CFU of *B. pertussis* strain Tohama in 20 μl of PBS. Six mice from cohorts of 12 mice were euthanized on each of days 3 and 7 post-infection. For cohorts of 24 mice, six mice were euthanized on each of days 3, 7, 10 and 14 post-infection. Lungs and trachea were aseptically excised from all euthanized mice, homogenized in PBS and plated to enumerate total bacteria present.

Statistics

Figure 2:
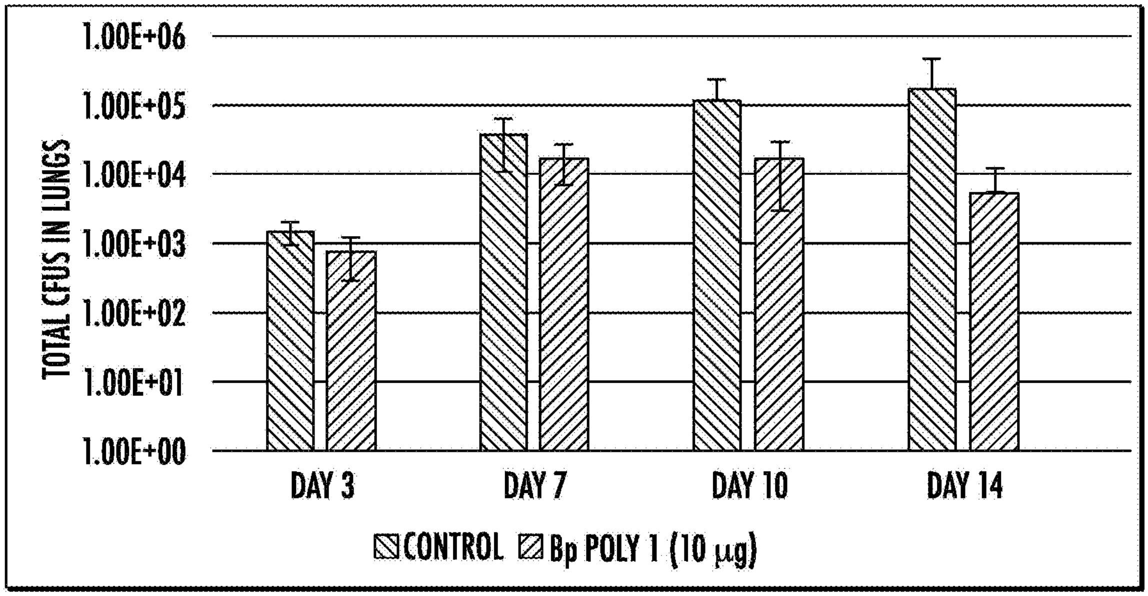
FIG. 2 depicts an experiment in which twenty-four mice are immunized with BpPoly1; final post-immunization bleed geometric mean titer 15.43. As illustrated, total colony forming units found in the lungs is less at 3, 10 and 14 days in immunized mice versus control mice.
Figure 3:
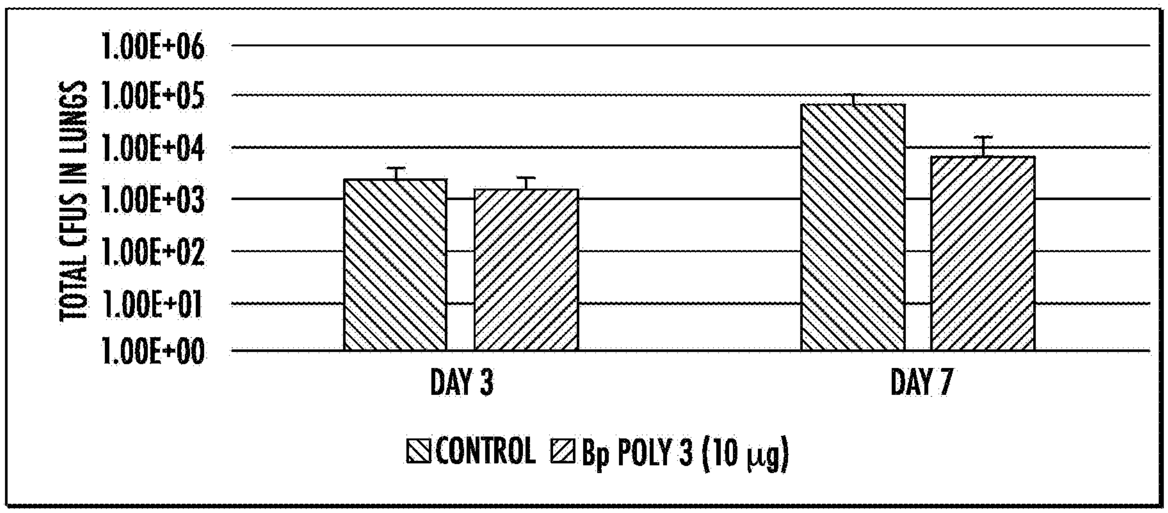
FIG. 3 depicts an experiment in which twelve mice immunized with BpPoly3; final post-immunization bleed geometric mean titer 16.39. As illustrated, total colony forming units found in the lungs is less at 3 and 7 days in immunized mice versus control mice.
Figure 4:
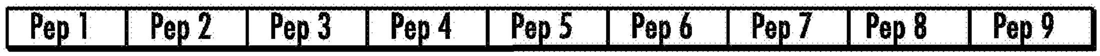
FIG. 4 depicts a schematic representation of a heterologous vaccine polypeptide using peptides derived from the sequences of peptide regions at different loci on the same protein and/or derived from different proteins within the same strain, species or organism.

Total bacterial counts in lungs were compared between groups using the Wilcoxon-Mann-Whitney test. See FIGS. 1-3. The immunogenicity of each Bp Polypeptides was analyzed in 12 mice to quantitate the serum titer of antibodies binding to the purified polypeptides. Anti-Bp Polypeptide antibody titers increased in every mouse against each Bp Polypeptide, demonstrating that each Bp was immunogenic in every mouse (see Tables 1 and 2, below). Post immunization antibody titers ranged from 1/200-1/51,200 for Bp Poly1 and 1/12,800-1/204,800 for Bp Poly3. ELISA signals of the preimmune sera were similar to background.

TABLE 1

ELISA Titers Post Immunization of Mice with 10 μg Bp Poly1

| Animal | Titer | log 2 titer |
|---|---|---|
| 04 B | 1/400 | 8.64 |
| 04 L | 1/51200 | 15.64 |
| 04 N | 1/800 | 9.64 |
| 04 R | 1/1600 | 10.64 |
| 05 B | 1/1600 | 10.64 |
| 05 L | 1/12800 | 13.64 |
| 05 N | 1/6400 | 12.64 |
| 05 R | 1/51200 | 14.64 |
| 06 B | 1/800 | 9.64 |
| 06 L | 1/1600 | 10.64 |
| 06 N | 1/1600 | 10.64 |
| 06 R | 1/200 | 7.64 |
| Av. Log2 titer | | 11.223333 |

TABLE 2

ELISA Titers Post Immunization of Mice with 10 μg Bp Poly3

| Animal | Titer | log 2 titer |
|---|---|---|
| 10 B | 1/204800 | 17.64 |
| 10 L | 1/102400 | 16.64 |
| 10 N | 1/102400 | 16.64 |
| 10 R | 1/102800 | 16.64 |
| 11 B | 1/12800 | 13.64 |
| 11 L | 1/102400 | 16.64 |
| 11 N | 1/204800 | 17.64 |
| 11 R | 1/102400 | 16.64 |
| 12 B | 1/102400 | 16.64 |
| 12 L | 1/51200 | 15.64 |
| 12 N | 1/102800 | 16.64 |
| 12 R | 1/51200 | 15.64 |
| Average log2 Titer | | 16.39 |

Example 2: Transcription Level (mRNA) as a Peptide Selection Criteria for Bacterial Vaccine Polypeptides (BVP) for *B. pertussis*

In our initial studies, putative vaccine peptides targeting *B. pertussis* were selected based on the following criteria: 1) Identification of the species conserved core of surface exposed proteins (SEPs) using the available *B. pertussis* genomes. These include secreted and surface exposed proteins embedded in the outer membrane as well as proteins located in the periplasmic space as the latter are variably expressed both on the surface and in the periplasm; 2) sequence conservation, based on analysis of multi-sequence alignments of each protein; 3) Surface exposure of the core proteins, based on in-silico modelling to determine the 3-dimensional structure and the potentially surface exposed residues. Using these criteria, a pool of approximately 150 peptides that are ≥20 amino acid residues in length have been identified for *B. pertussis*. From these a single Bacteria Vaccine Polypeptide (BVP) was previously designed with a random assortment of peptides. This BVP, Bp Poly 1 was shown to be significantly protective in the mouse lung model (data not shown).

To further refine the selection of peptides, we investigated the relative abundance of gene specific mRNA in whole RNA transcriptomic studies to determine whether high level transcription, which generally correlates with the quantity of protein produced in bacteria, may be a useful criterion to identify protective targets. Such an approach has several advantages. Public databases contain many transcriptomic studies for many pathogens. With the advent of RNA-seq the data is high quality and accurately reflects the total RNA profile. RNA-seq also allows for small sample sizes, unlike the older micro-array data which required larger quantities of starting bacteria. Therefore, there are now multiple sources for quantitative transcription data, enhancing the availability of a possibly important vaccine peptide criteria. To investigate this criteria, we designed a polypeptide (Bp Poly 100) using peptides with the above criteria and derived from genes with low level transcription. We also designed a polypeptide (Bp Poly 101) using peptides with the above criteria and derived from genes with high level transcription. Each polypeptide was purified and their protective capacities were compared in the mouse model of pertussis.

Design of Bp Poly 100 and Bp Poly 101

To test whether transcription level may be useful for selecting protective peptides, Bp Poly 100 and Bp Poly 101 were designed using a final step of prioritization of the vaccine peptide selection based on transcriptomic data indicated by quantitative mRNA. We used the publicly available data from de Gouw et al[1] with relative mRNA abundance of the *B. pertussis* transcriptome to analyze the individual relative abundance of each protein identified. Using our defined core of SEP genes, the individual relative abundance (RA) of each was determined, based on the data of de Gouw et al[1]. Proteins in commercially available *B. pertussis* vaccines were excluded. The peptides from proteins with the lowest RA of mRNA (values range 29-374) were incorporated into Bp Poly 100. The peptides from proteins with the highest RA of mRNA (values range 11,819-47,656) were incorporated into Bp 101 (See FIGS. 6 and 7). The entire range of RA of mRNA as determined by de Gouw et al. is from 0 to 52,549 for the maximally expressed secreted protein, ptxA. DNA encoding Bp Poly 100 and Bp Poly 101 were independently incorporated into a pET100 expression vectors downstream of the His-tag to facilitate purification. Each polypeptide was purified by standard nickel affinity chromatography.

Protection of Bp Poly 100 vs. Bp Poly 101

Testing of Bp Poly 100 vs. Bp Poly 101 for protection in the mouse model of Pertussis was performed as previously established in the field[2]. Each mouse in three groups received adjuvant (alum+mPLA) alone, adjuvant with 10 µg Bp Poly 100, or adjuvant with 10 µg Bp Poly 101 per immunization. Immunizations were performed at T-0, T-2 weeks, and T-4 weeks. Three weeks later, the animals were infected by nasal aspiration of 7.9E+03 CFU of the *B. pertussis* Tohama I strain in 20 uL PBS. On days 3, 7, and 10 after infection, a subgroup of animals was sacrificed, and the homogenized lungs were quantitatively cultured.

Results

Bp Poly 101 (High Level Transcription) was More Protective than Bp Poly 100 (Low Level Transcription).

Figure 7:
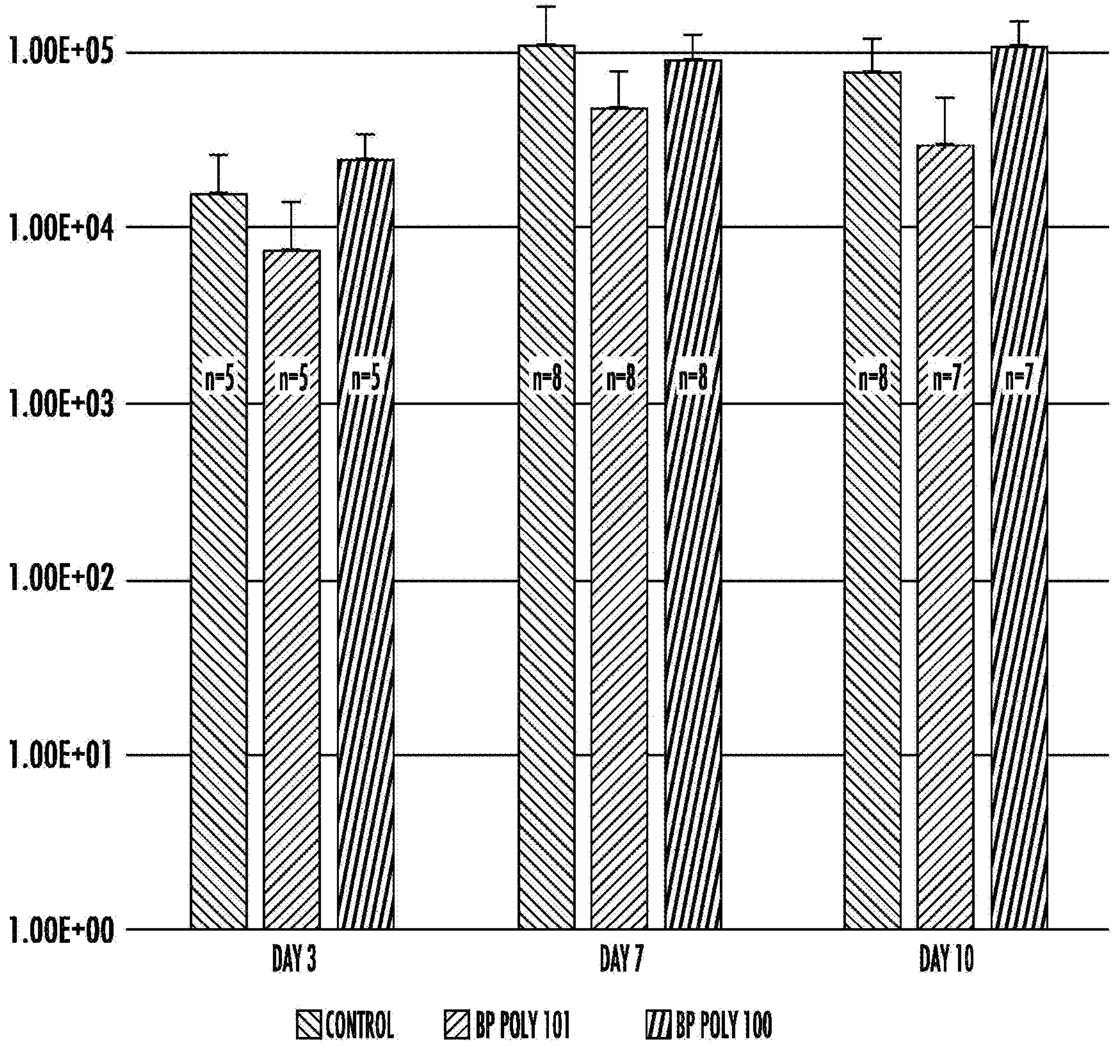
FIG. 7 depicts bacterial titers in the lungs of mice infected with *B. pertussis* strain Tohama. Control. The number inside the bar refers to the number of animals in each cohort at each time point.

To test whether the quantity of mRNA transcripts may be useful in selecting among peptides for inclusion in a BVP, two BVP were designed and compared. Bp Poly 100 consisted of peptides in proteins encoded by genes with low levels of mRNA, and Bp Poly 101 consisted of peptides in proteins encoded by genes with high levels of mRNA. Protection was compared in the mouse model of pertussis. FIG. 7 shows the results of quantitative cultures of homogenized mouse lungs at days 3, 7, and 10 after infection. The Table shows the p values resulting from the statistical analysis of the data.

TABLE 3

Statistical significance of quantitative cultures from control, Bp Poly 100, and Bp Poly 101 groups over the period of the experiment. P values between the three experimental conditions were determined by Wilcoxon-Mann-Whitney test.

| Day | Bp Poly 100 vs. control | Bp Poly 101 vs control | Bp Poly 101 vs. Bp Poly 100 |
|---|---|---|---|
| Day 3 | 0.92 | 0.15 | 0.016 |
| Day 7 | 0.48 | 0.034 | 0.013 |
| Day 10 | 0.90 | 0.01 | 0.002 |

On no day was there a significant difference between the quantity of bacteria from the group receiving Bp Poly 100 compared to the control group. In contrast, the number of bacteria isolated from the group receiving Bp Poly 101 was significantly less than from the control group on Days 10 and 14. Similarly, the number of bacteria isolated from the group receiving Bp Poly 101 was significantly less on Days 3, 10, and 14 compared to the group receiving Bp Poly 100.

Conclusion

The data show that Bp Poly 101, consisting of peptides from proteins encoded by genes with high level transcription, demonstrated significantly better protection at each time point than either the control group (adjuvant alone) or Hi Poly 100, consisting of peptides from proteins encoded by genes with low-level transcription. Previous work showed that peptides in proteins present throughout the species, sequence conserved, and surface exposed based on in-silico.

Example 3: Antisera Against Hi Poly 1 Binds to *Haemophilus influenzae* Strains Representative of the Species We have proposed the Bacterial Vaccine Polypeptide (BVP) methodology based on the selection of peptides that are present in all strains in the species, sequence conserved, and exposed to the surface based on in-silico protein structure analysis. Using *Haemophilus infuenzae*, we selected a subgroup of peptides that were individually protective in the infant rat model of bacteremia. In order to enhance immunogenicity, the peptides are presented as linked in a polypeptide.

Because of the multi-targeted design, the polypeptide would be expected to stimulate antibodies that bind to every strain in the species. To empirically analyze of the binding range of antibodies, we used strains in a Live Cell ELISA that were previously characterized to represent the breadth of the species.

Materials and Methods

*H. influenzae* strains. Musser et al. previously characterized the genetics of a large number of *H. influenzae* strains by multi-locus enzyme electrophoresis. We tested 9 of the Musser strains that were representative of the genetic breadth of the species. These nontypable strains, isolated from children with OM were HI1371, HI1375, HI1380, HI1387, HI1392, HI1397, HI1403, HI1417, and HI1425. We also tested two capsulated type b strains, E1A and H10693.

Bacterial Growth. Isolates were routinely maintained on chocolate agar with bacitracin at 37° C. Broth cultures of *H. influenzae* were grown in brain heart infusion (BHI) agar supplemented with 10 μg/ml heme and 10 μg/ml β-NAD (supplemented BHI; sBHI).

Generation of anti-HI Poly 1 antisera. The Hi Poly 1 was purified by nickel chromatography and adsorbed to alum (1:1) and used as an immunogen to generate anti-sera in rats. Prior to the immunization, blood was taken from each animal (pre-immune sera, PIS). Three doses of Hi Poly 1 were administered at 2-week intervals, and anti BVP Hi Poly 1 post-immune sera (BVPS) collected three weeks after the final immunization. Sera samples were heat-inactivated and stored at −80° C.

Live Cell ELISA. Live cultures of *H. influenzae* were used in a whole cell ELISA. Overnight bacterial suspensions were diluted to give an $OD_{600}$ of 0.05 and 100 μl added to wells of a Corning high binding, 96-well plate. The plate was gently centrifuged and the bacteria allowed to adhere for 4 hrs at 4° C. Following incubation, the supernatant was aspirated and the adhered bacteria washed and incubated with either the rat pre-immune sera (PIS) or post immune sera (BVPS) as the primary antibody. Adherence of the primary antibody was detected with HRP-conjugated goat-anti-rat antisera as directed by the manufacturer. Bound secondary antibody was quantified by the addition of 100 μl TMB and the plates were read at $A_{450}$. Each assay was performed in triplicate and the values averaged.

Statistics. The mean absorbance values resulting from matched pre- and post-immune sera for each isolate were compared using Student's T test.

Results

Figure 8:
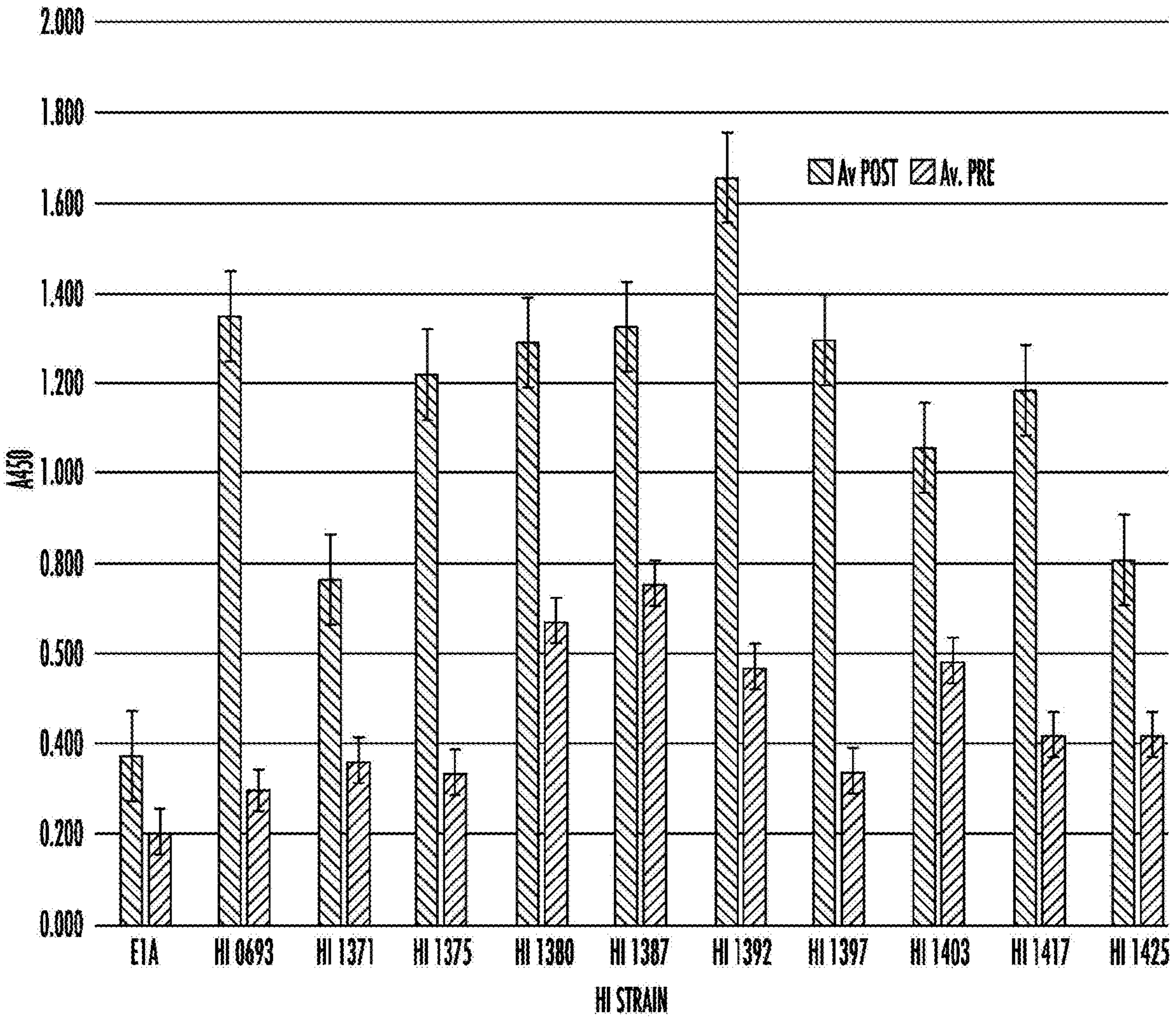
FIG. 8 depicts live cell ELISA of 12 *H. influenzae* strains using pre- and post-immune sera from rats immunized with the BVP Hi Poly 1.

The results (FIG. 8) show that the absorbance resulting from binding of antibodies in the pre-immune sera ranged from 0.20 to 0.75. The absorbance resulting from binding of antibodies in the post-immune antisera ranged from 0.375 to 1.658. For each of the 12 HI isolates examined, the results using post-immune antisera (BVPS) were greater than results using the matched pre-immune sera (PIS). With each strain, the differences between the PIS and BVPS absorbance were statistically significant ($p<0.05$).

Conclusions

The BVP methodology proposes that linked peptides may be useful to deliver specifically identified peptides with important vaccine characteristics, including presence across the species, sequence conservation, and surface exposure based on in-silico protein structural analysis. The identification of peptides that induce passive (antibody) protection provided an opportunity to empirically test the hypothesis that the linked peptides would induce antibodies that bind strains representative of the species. Our data demonstrating significantly greater binding in post-immune anti Hi Poly 1 antisera support the hypothesis. The presence of significantly greater binding of post-immune antisera to the encapsulated type b strains raises the intriguing possibility of Hi Poly 1 as a vaccine protecting against both type b strains and nontypable *H. influenzae*. These data support the utility of the Bacterial Vaccine Polypeptides methodology and support Hi Poly 1 as a vaccine candidate.

Example 3: Methods of Making a Bacterial Vaccine Polypeptide Protective Against Nontypable *Haemophilus* Influenza NTHi remains a significant public health burden and an appropriate target for vaccine development.

Various NTHi surface proteins have been proposed as vaccine candidates. One of these proteins, Protein D, was tested in clinical trials and found to be approximately 35% effective in preventing NTHi OM and is commercially available in Europe. In addition to its relatively low effectiveness, Protein D is also not present in every clinical isolate of NTHi. Therefore, other approaches to NTHi vaccines, including approaches with multiple targets, should be considered.

As an alternative to full-length proteins as vaccines, we propose a novel method that integrates genomic bioinformatics and in silico structural predictions to map the surface of NTHi to identify sequence-conserved, surface-exposed regions (peptides) of proteins encoded by multiple genomic loci. Evidence of passive protection was used as a further selective criterion confirming surface exposure and antibody accessibility.

Unfortunately, previous efforts to use peptides as bacterial vaccines have not been successful. One common barrier to the use of peptides in vaccines is the lack of sequence conservation, e.g. pili vaccines. Thus, pili peptide vaccines are effective against homologous strains and ineffective against other strains of the same species with nonhomologous pili. In addition to the lack of sequence conservation in proposed peptide vaccines, the small size of peptides correlates with lower immunogenicity. The smallest commercially available vaccine is the 24 KDa Hepatitis B surface antigen (HBsAG), and smaller peptides are usually linked to carriers for immunogenicity in preclinical studies.

To address these issues, we hypothesized that a BVP consisting of linked sequence-conserved, surface-exposed peptides from multiple genomic loci would be immunogenic and biologically effective in an established animal model of otitis media. Thus, we designed NTHi Vaccine Polypeptide Hi Poly 1 from peptides shown to be individually biologically effective, and we tested Hi Poly 1 for immunogenicity, protection in the infant rat model of bacteremia, and effectiveness in the chinchilla (*Chinchilla lanigera*) model of OM.

Materials and Methods

Bacterial Strains and Growth Conditions

The NTHi strain R2866 was isolated from the blood of an immunocompetent child with clinical signs of meningitis subsequent to OM and characterized by Arnold Smith [21]. We have previously utilized this strain in the infant rat model of invasive *H. influenzae* disease. NTHi strain 86-028NP used in the *chinchilla* (*Chinchilla lanigera*) model of otitis media is a minimally passaged clinical isolate from a pediatric patient who underwent tympanostomy and tube insertion for chronic otitis media at Columbus Children's Hospital. Strain 86-028NP has been extensively characterized in chinchilla models of OM. We and others have previously used this isolate in numerous studies on the virulence of NTHi in chinchillas. Isolates of *H. influenzae* were routinely maintained on chocolate agar with bacitracin at 37° C. Broth cultures of *H. influenzae* were grown in brain heart infusion (BHI) agar supplemented with 10 μg/ml heme and 10 μg/ml β-NAD (supplemented BHI; sBHI).

*Escherichia coli* isolate BL21(De3) was routinely maintained on LB agar and isolates transformed with plasmid pHiPoly1 were maintained on LB agar supplemented with 50 µg/ml of carbenicillin.

Hi Poly 1 Design

Figure 9:
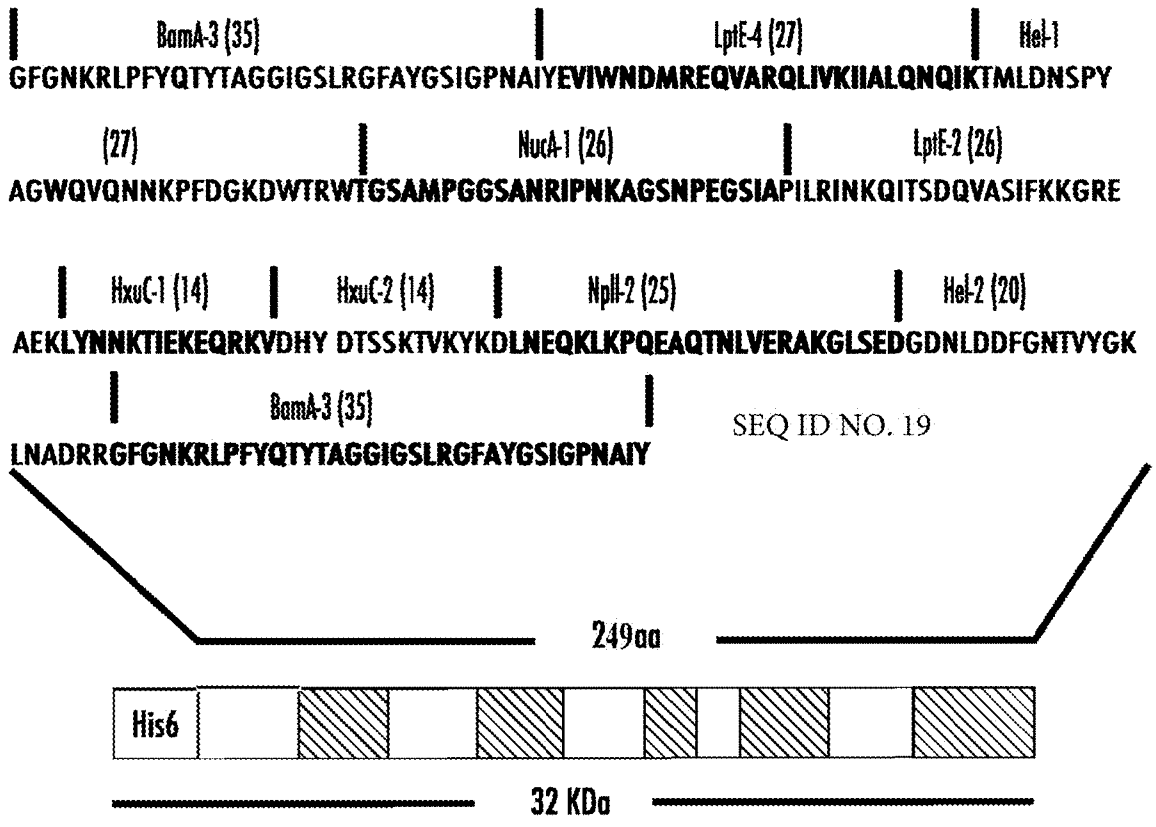
FIG. 9 depicts composition of the Bacterial Vaccine Polypeptide Hi Poly 1. Hi Poly 1 was designed as a linear sequence of *H. influenzae* peptides with BamA-3 at each terminus with a His-Tag at the N-terminus as shown. The length in amino acids of the combined *H. influenzae* peptides and the overall size are indicated.

We previously reported the methodology for the selection of certain NTHi candidate vaccine peptides, including Hel1, HxuC1, HxuC2, and Hel2, based on their 1) presence in each examined genome; 2) surface exposure based on structural analysis; 3) sequence conservation; and 4) induction of antibodies protective in the infant rat model of bacteremia [17]. Following the same methodology, we identified other peptide candidates that showed protection in the infant rat model of bacteremia (data not shown), including NucA-1, BamA-3, Lpte-2, Lpte-4 and NlpI-2. The bacteria vaccine polypeptide, Hi Poly 1, was designed as a sequential assembly of the 9 peptides with peptide BamA-3 at each end to enhance immune processing and a 6His tag at the N terminus (FIG. 9).

Hi Poly 1 Purification

An expression vector was commercially manufactured by Invitrogen to express the Hi Poly 1 polypeptide. The DNA encoding the construct was optimized for *E. coli*, synthesized, and the correct sequence confirmed prior to insertion in to the pET100 expression vector downstream of the His-tag. The plasmid construct (pHiPoly1) was transformed into *E. coli* BL21(De3) and transformants were selected on LB agar supplemented with 50 µg/ml of carbenicillin, and transformed strains were stored at −80° C. Select transformants were further examined to ensure insertion of the correct DNA sequence. *E. coli* containing pHiPoly1 were inoculated into LB broth supplemented with 1% glucose in addition to carbenicillin and grown to an optical density of approximately 0.5-0 at $A_{600}$ at 37° C. Expression of pHiPoly1 was induced by the addition of IPTG to 1 mM for 4 hours. Bacterial pellets were prepared by centrifugation at 4500 rpm for 15 minutes, and the pellets were examined for expression of the bacterial vaccine polypeptide against an uninduced negative control. SDS-PAGE of cell fractions indicated that Hi Poly 1 was expressed as an inclusion body. Bacterial pellets containing the Hi Poly 1 inclusion bodies were lysed in 10 ml of Cell Lytic TM B buffer (Sigma) supplemented with Benzonase (50 units/ml final) and lysozyme (0.2 mg/ml final) (Sigma). Following a one-hour incubation at room temperature with gentle shaking, the inclusion bodies were pelleted by centrifugation for 20 minutes at 16,000×g at 4° C. The pellet containing the Hi Poly 1 polypeptide was dissolved in 6M Guanidine Hydrochloride, 20 mM, sodium phosphate pH 7.8 and 0.5 M NaCl followed by a further centrifugation at 16,000×g to remove insoluble impurities. Purification of the Hi Poly 1 Vaccine Polypeptide was accomplished using His-Tag affinity through a pre-equilibrated $Ni^{+2}$ affinity column as directed by the protocol of ProBond™ purification system (Life technologies) under denaturing conditions. The Hi Poly 1 was eluted from the $Ni^{+2}$ column with 300 mM imidazole in binding buffer, and elution fractions were collected for analysis of protein content and purity. Purified Hi Poly 1 was adsorbed to AdjuPhos (1:1) by incubating the mixture with gentle mixing for 2 hours at room temperature. The adsorbed mixture was dialyzed against PBS at 4° C. The relative adsorption of Hi Poly 1 to AdjuPhos was determined by measuring the protein concentration of the supernatant of the centrifuged preparation. Alum adsorbed Hi Poly 1 was stored at 4° C. until use.

ELISA

ELISAs were performed following the specific protocols of the respective manufacturers. Peptide ELISAs utilizing peptides synthesized with an N-terminal Cys residue were performed in maleimide activated plates (Pierce). Specific peptides were dissolved at 1 mg/ml in 20% dimethyl formamide, 10% TCEP in binding buffer, and subsequently diluted to a concentration of 5 µg/ml with binding buffer. One hundred microliters of the peptide solution was added into each well, and the peptides immobilized by incubating the plate overnight with gentle shaking at 4° C. Plates were blocked by the addition of 200 µl of cysteine solution (10 µg/ml) for 1.5 h at room temperature. ELISAs against the his-tagged Hi Poly1 were performed in Corning high binding plates. The vaccine polypeptide, Hi Poly 1 was solubilized in 4M urea, 0.05M Carbonate buffer, pH 9.6, at a concentration of 20 µg/ml. To each well, 100 µl was added and the plate incubated overnight at 4° C. to immobilize the polypeptide. In each ELISA, chinchilla sera were used as the primary antibody and goat anti-rat HRP-conjugated IgG used as a secondary. Bound secondary antibody was detected by the addition of 100 µl TMB and the plates were read at $A_{370}$. The determined titer was the final antibody dilution with the absorbance of the post immune antisera greater than 0.1 compared to the preimmune sera.

Animals

Animal studies were peformed in accordance with the recommendations in the Guide for the Care and Use of Laboratory Animals of the National Institutes of Health and were approved by the Institutional Animal Care and Use Committees of Arizona State University (chinchilla studies) and The University of Arizona (infant rat studies).

Infant Rat Model of Bacteremia

Protection by Hi Poly 1 in the infant rat model of passive protection was tested as previously described. Pre- and post-immunization sera samples, derived from immunized chinchillas were used to passively immunize infant rats. Two-day old pups were randomly reassigned to the dams to give three cohorts of 10 pups each. At four days of age, the infants in each cohort variously received 100 µl IP injection of either pre-immune chinchilla sera, post-immune sera or PBS as a control. At 5 days of age each pup was challenged by IP injection of approximately $1.5\times10^5$ CFU NTHi strain R2866 in 50 µl PBS. At 24 h post challenge, blood was collected from each animal for quantitative plating.

Chinchilla Model of Otitis Media

To test the protective effectiveness of Hi Poly 1 in OM, three- to five-month-old chinchillas (*Chinchilla lanigera*) were purchased from Moulton Chinchilla Ranch. Animals were rested for at least 7 days upon arrival to acclimate prior to initiating the study. Animals with no evidence of middle ear infection by either otoscopy or tympanometry upon initiation of the study were used as previously described. Preliminary experiments were performed to determine the optimal dose for immunizing chinchillas with Hi Poly 1. The purified Hi Poly 1 protein mixed with 1:1 with alum adjuvant was used to immunize cohorts of chinchillas at 10, 50, 100, 200 and 400 µg doses (3 animals per cohort). Animals were immunized three times at two-week intervals and sera samples taken three weeks after the last boost. Sera were collected and used in an ELISA with the Hi Poly 1 or the individual peptides as antigens. Hi Poly 1 was immunogenic, and doses of 200 µg induced a demonstrable increase in IgG against the polypeptide and all the individual peptides compared to pre-immune sera (data not shown). The dose of 200 µg per immunization was used in the protection studies.

Two immunization/protection chinchilla experiments were performed. In the first experiment, cohorts consisted of 18 animals in the test and control groups; a repeat study consisted of 23 animals in control group and 22 in vaccine group (the vaccine cohort originally contained 23 animals; however, one animal was removed from the study during the immunization phase due to non-protocol related health issues). The immunizations, infection challenges, and tests for OM were identical for the two experiments, and the data were pooled for analysis.

Bacterial Challenge

The cohorts of chinchillas were immunized three times at 2-week intervals with either 200 μg Hi Poly 1 with alum or PBS-alum. Antisera from samples taken pre-immunization and 2 weeks following the last immunization of each animal were heat inactivated and stored at −80° C. until examination of antibody titers by ELISA and use in the infant rat model of passive protection. Three weeks after the last immunization, each chinchilla was challenged in both ears with approximately 1500 CFU of NTHi strain 86-028NP in 300 μl PBS-gelatin (0.1% w/v) by direct injection of bacterial suspensions into the superior bullae. Challenge dosages were confirmed by plate count.

Examination for Evidence of Otitis Media

Prior to direct infection and on days 3, 7, 10, and 14 days post challenge, each chinchilla was examined by video otoscopy and tympanometry for evidence of OM; a subset of each cohort, was examined for middle ear effusion (MEE) and removed from the study. Signs of tympanic membrane inflammation by video otoscopy (Video VetScope System, MedRx, Seminole, FL, USA) were rated on a 0 to 4+ scale as previously described. As each ear was examined, the video otoscopy was recorded and graded 0-4 based on visible erythema, bulging, changes in opacity of the tympanic membrane, and visualization of effusion behind the tympanic membrane. Individual ears scored at ≥2 were considered positive for OM. The recorded video otoscopy was evaluated by a second blinded observer. Differences between the first and second evaluation were blindly resolved, including a third blinded observer. Tympanometry (EarScan, South Daytona, FL, USA) was used to monitor changes in both tympanic width and tympanic membrane compliance, as previously described. Using tympanometry, compliance or height of the tympanogram measures the impedance of the tympanic membrane, and is expressed in milliliters of equivalent volume. Abnormal compliance outside the 0.75-1.5 range was considered evidence of OM. Similarly, the width and overall shape of the tympanogram is a useful indicator of OM, and tympanometric width (TW) greater than 150 daPa was considered evidence of OM. MEE were collected by trans-bullar tap to withdraw fluid from the middle ear cavity using a 1.5 inch 25-gauge hypodermic needle. If no MEE was detected, the same ear was tapped a further two times to ensure the absence of MEE. Such ears were scored as "dry". Bacterial titers in MEE were determined using the track dilution method as previously described.

Statistical Analysis.

Data from chinchilla experiments 1 and 2 were pooled for each outcome at each time point (day post infection) measured. The proportion of otoscopy, tympanometry, and presence of MEE on each day were compared between vaccinated and control groups using the Fisher exact test. Quantitative measures, including CFU/ml in MEE in chinchillas and blood in the infant rat model were compared between vaccinated and control groups using the Kruskal-Wallis test. Sensitivity analyses examined dry ear MEE imputed as 0 CFU/ml. Bacterial titers in MEE were analyzed using the Wilcoxon-Mann-Whitney test. Statistical analyses were performed using the SAS software, version 9.2 (SAS Institute Inc., Cary, North Carolina). All statistical tests were 2-sided, with significance evaluated at the 5% level.

Results

Hi Poly 1

The sequential arrangement of the 9 unique peptides from 6 proteins is shown in FIG. 1. The resulting 249 amino acid construct was calculated to have a theoretical molecular weight of 27,724 Da (31,844 with the His-tag) and a pI of 9.57 (9.71 with the His-tag).

Figure 10:
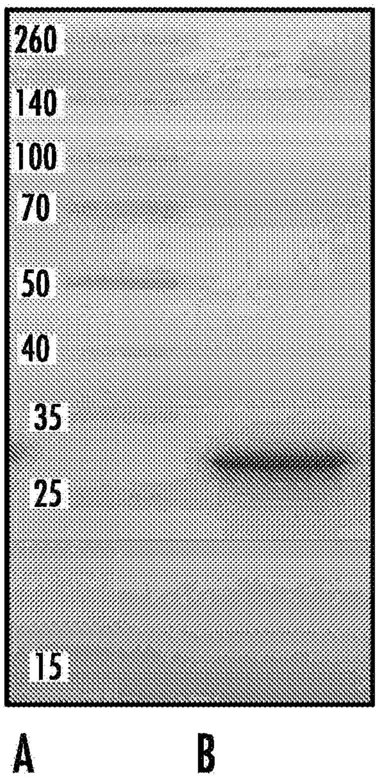
FIG. 10 shows an SDS-PAGE of purified Hi Poly 1. Hi Poly1 was eluted from a nickel affinity column and a fraction of the eluate examined by denaturing SDS-PAGE. Molecular weight markers (lane A) were used to estimate the size of the polypeptide (Lane B).

After affinity purification, the purity of Hi Poly 1 was analyzed by SDS-PAGE (FIG. 10); a single protein band correlated with the theoretical MW of 32 KDa. This preparation of Hi Poly 1 was adsorbed 1:1 to Adju-Phos.

Immunogenicity of the Hi Poly1 Vaccine Polypeptide.

Figure 11:
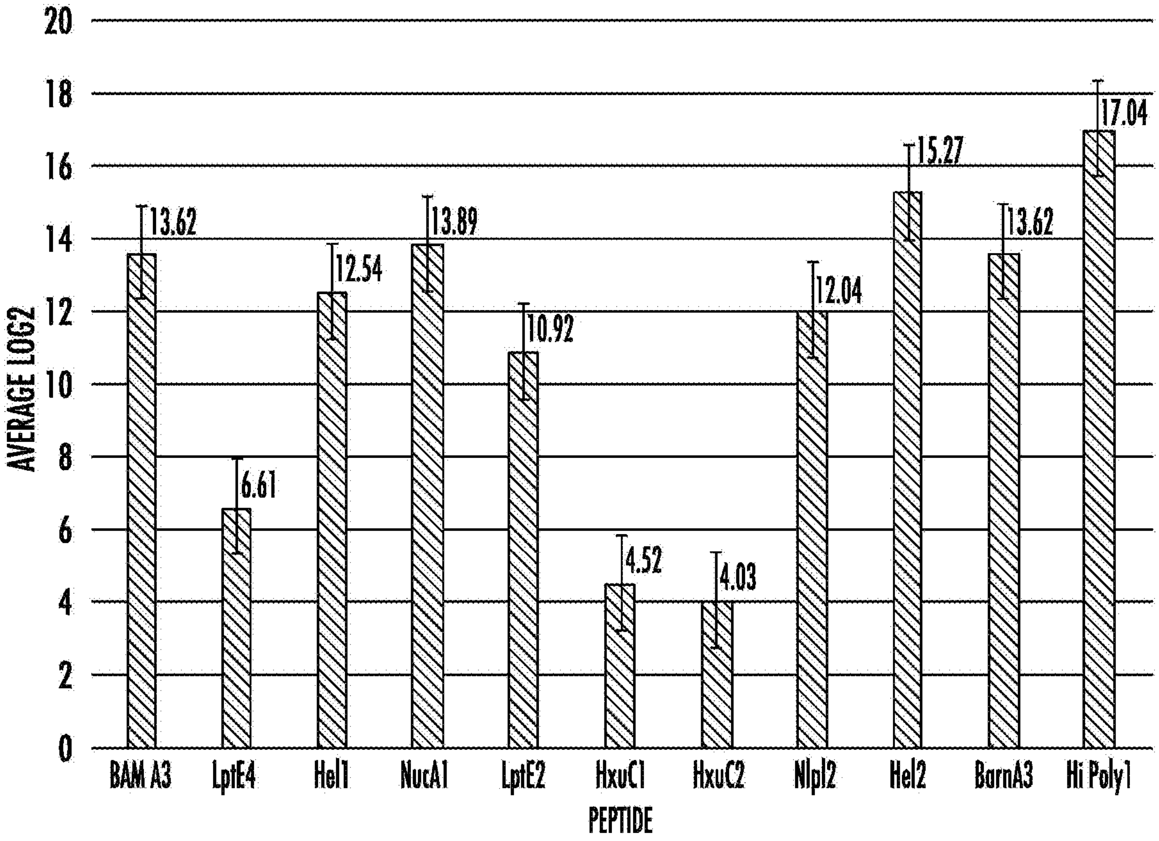
FIG. 11 depicts an ELISA of antisera from chinchillas immunized with Hi Poly 1. Antisera were tested against the whole polypeptide and the individual component peptides (data are shown in the same order as the order of the peptides in HiPoly1). Average log 2 transformed titers of the 40 chinchilla antisera samples collected 14 days after the final immunization with Hi Poly 1.

Control, pre- and post-immunization sera were examined for antigen specific IgG by ELISA. The antibody titer indicated that immunization with Hi Poly 1 resulted in a strong and reproducible immune response to the polypeptide in each of the 40 animals ($log_2$ titer average 17.04) while antisera from pre-immunized and control animals were at background levels ($log_2$ titer ≤1.0) (FIG. 11). Using the Hi Poly 1 as an immunogen, the immune response to each of the component peptides was meaningful, with a $log_2$ titer average increase of ≥4, varying between 4.03 and 15.27. In each experimental vaccine group, the lowest response was to the two peptides from HxuC. Several animals failed to elicit a measurable immune response to one and/or the other HxuC peptides. Of the 40 animals receiving Hi Poly 1, 13 and 18 of them did not show a significant increase in antibody titers to HxuC-1 and HxuC-2, respectively. Additionally, 10 animals did not have a significant increase in antibody titer to LptE-4. In contrast, the titers to the other components were high, in the 11-15 range.

Protection Against Bacteremia

Figure 12:
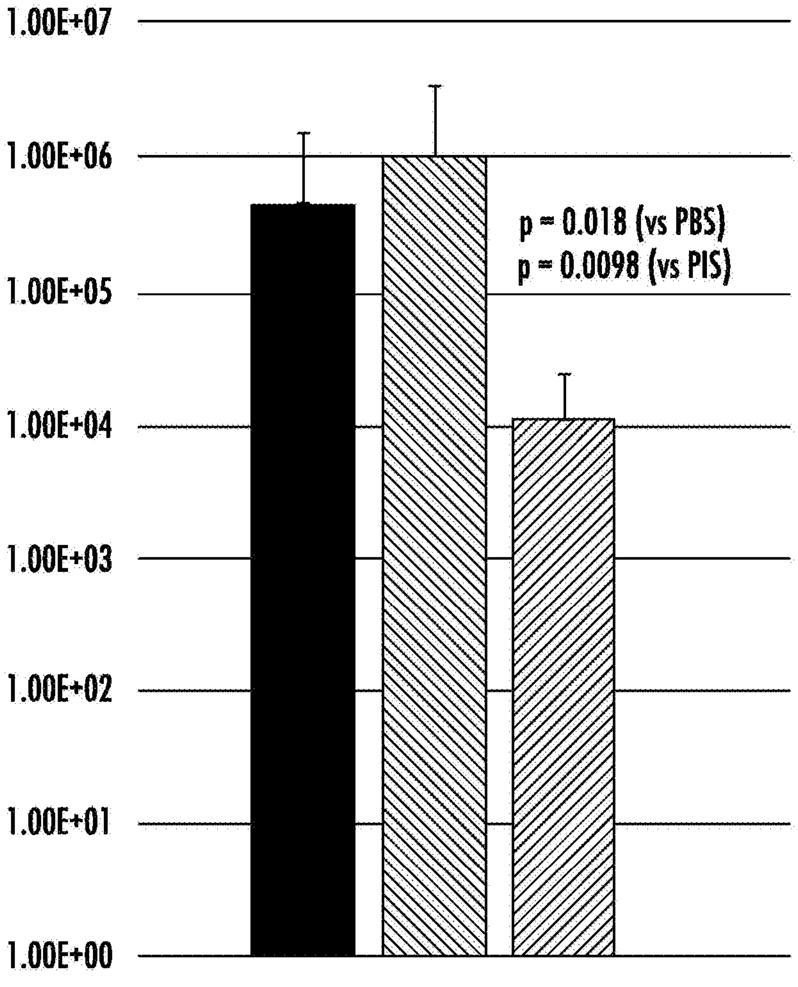
FIG. 12 demonstrates that protection is afforded by antisera raised against Hi Poly 1. Protection was determined in the infant rat model of bacteremia. Infant rats were treated with chinchilla anti-HiPoly1 BVP antisera (BVP) matched pre-immune sera (PIS) or PBS. Twenty-four hours later all rats were challenged with NTHi strain R2866 and a further 24 hours later bloods were collected for determination of bacteremic titers. Using the Wilcoxon-Mann-Whitney test to compare bacteremic titers (mean±SD) p=0.018 for PBS vs BVP and p=0.0098 for PIS vs BVP.

To investigate the protective capacity of Hi Poly 1 in bacteremia, chinchilla post-immunization antisera were compared to PBS and pre-immunization chinchilla sera for passive protection of infant rats against strain NTHi 2866 (FIG. 12). There was no detectable difference in the protection between PBS and pre-immune sera. Post-immune antisera significantly reduced bacteremia compared to either PBS or pre-immune sera (p=0.018 and 0.0098 resp.).

Protection in Otitis Media

Twenty-one days after the last immunization, chinchillas were transbullarly inoculated with NTHi 86-028NP in 300 μl of PBS. Quantitative counting of the inoculum confirmed that in both experiments, approximately $1.4\times10^3$ CFU were instilled into each bulla.

Figure 13:
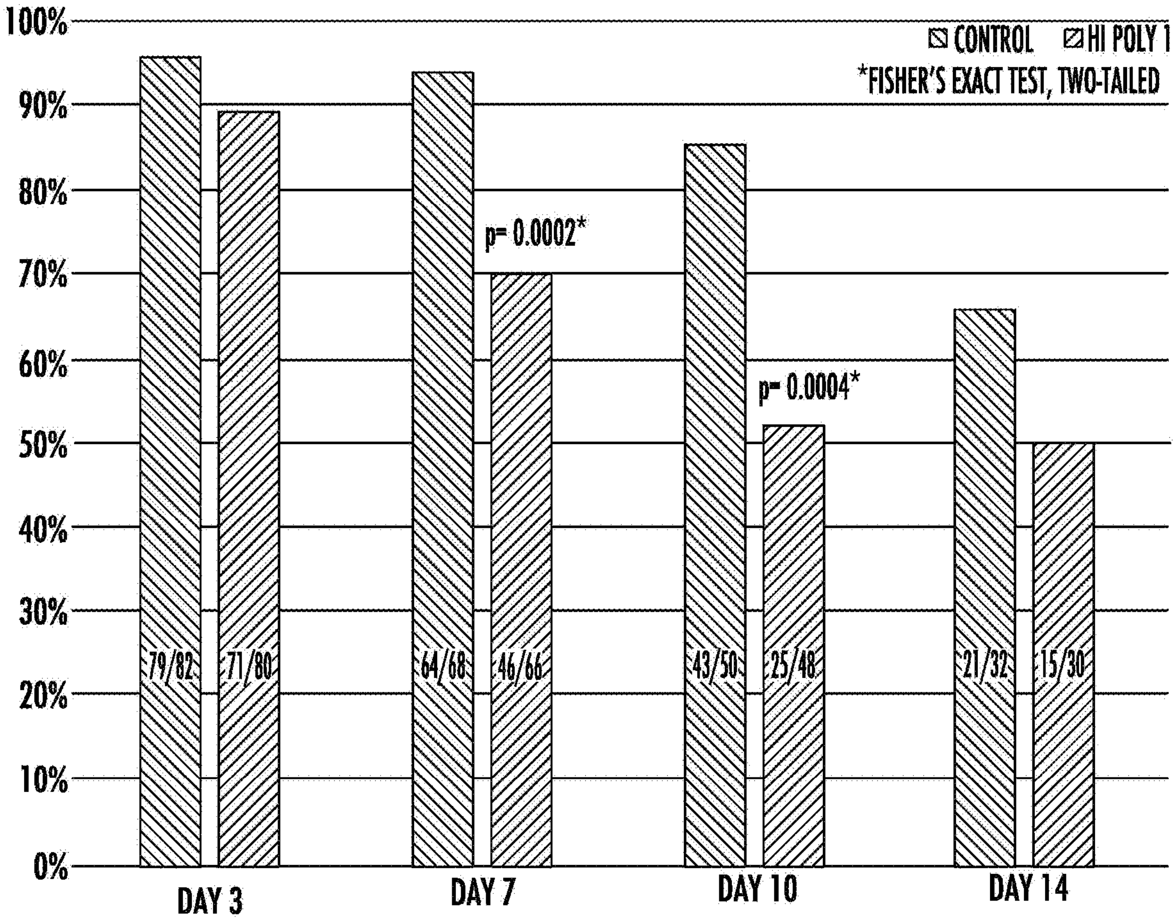
FIG. 13 depicts tympanometric assessment of OM in chinchillas challenged with NTHi 86-028NP. The percentage of ears determined by tympanography to be positive for otitis media based on tympanic width and compliance are shown. Control chinchillas (immunized with adjuvant alone) are shown and chinchillas immunized with the BVP Hi Poly 1 are shown. Tympanometry was performed on days 3, 7, 10, and 14. Using Fisher's exact test, there was a statistically significant difference between control and BVP animals on days 7 and 10 (p=0.0002 and 0.0004 respectively). The number inside the bar refers to the number of positive ears and the total cohort size examined).

The tympanogram measurements revealed a significant decrease in OM positive ears in the Hi Poly 1 treated group compared to the control group over the 14 days of the experiment (FIG. 13). Early after challenge on day 3 post inoculation, 96% (79 of 82) of the ears of the control animals had clinical signs of OM and 89% (71 of 80) of the Hi Poly 1 immunized animals had OM. By day 7, there was a statistically significant difference between the two cohorts; 70% (46 of 66) of the Hi Poly 1 group had OM while 94% (64 of 68) of the control group were positive for OM (p=0.0002). This difference continued at day 10 with 52% (25 of 48) of the vaccine group and 86% (43 of 50) of the control group with evidence of OM (p=0.0004). On day 14 post inoculation, the control group had begun to clear the infection; 50% of the vaccine cohort had OM and 66% of the control group had OM.

Figure 14:
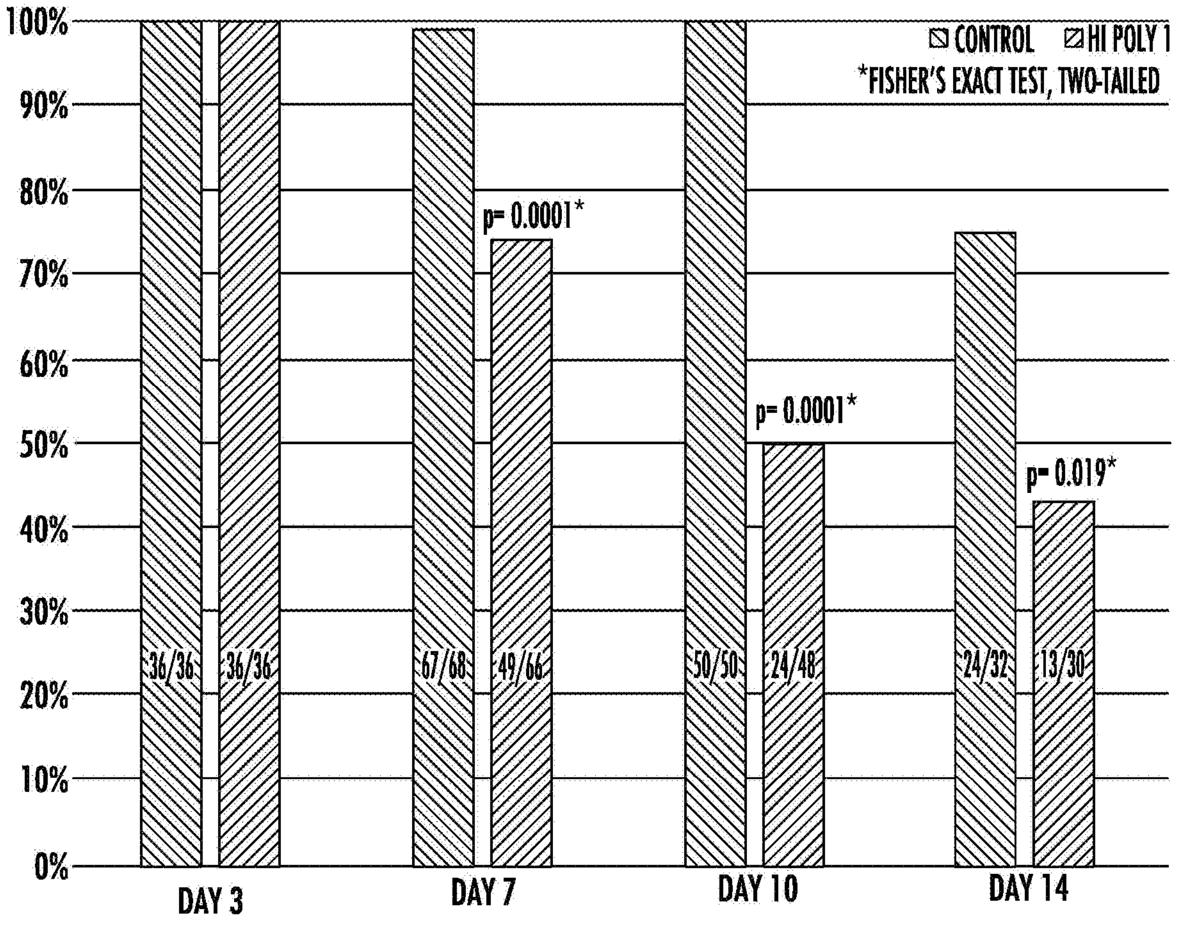
FIG. 14 depicts blinded video otoscopic assessment of otitis media in chinchillas challenged with NTHi 86-028NP. The percentage of ears determined by blinded otoscopy to be positive for otitis media are shown. Control chinchillas (immunized with adjuvant alone) are shown and chinchillas immunized with Hi Poly 1 are shown. Otoscopy was performed on days 3, 7, 10, and 14. Using Fisher's exact test, there was a statistically significant difference between control and BVP animals on days 7, 10 and 14 (p=0.0001, 0.0001 and 0.019 respectively). The number inside the bar refers to the number of positive ears and the total cohort size examined.

Similar to the tympanometry data, video otoscopy at day 3 showed that all ears had evidence consistent with OM (FIG. 14). On day 7, 99% (67 of 68) of the control group were defined as positive for OM while 74% (49 of 66) of the vaccine group were OM positive (p=0.0001). On day 10, 100% (50 of 50) of the ears of animals in the control group were positive for OM; only 50% (24 of 48) of the ears of animals in the vaccine group were OM positive (p=0.0001). By day 14, the control group had begun to show clearance of disease and 66% (24 of 32) of ears showed signs of OM while the vaccine cohort had decreased to 43% (13 of 30) positive for OM (p=0.019). Both the tympanometry and video otoscopy data indicate that the vaccine treated animals showed a more rapid clearance of disease compared to the controls.

Figure 15:
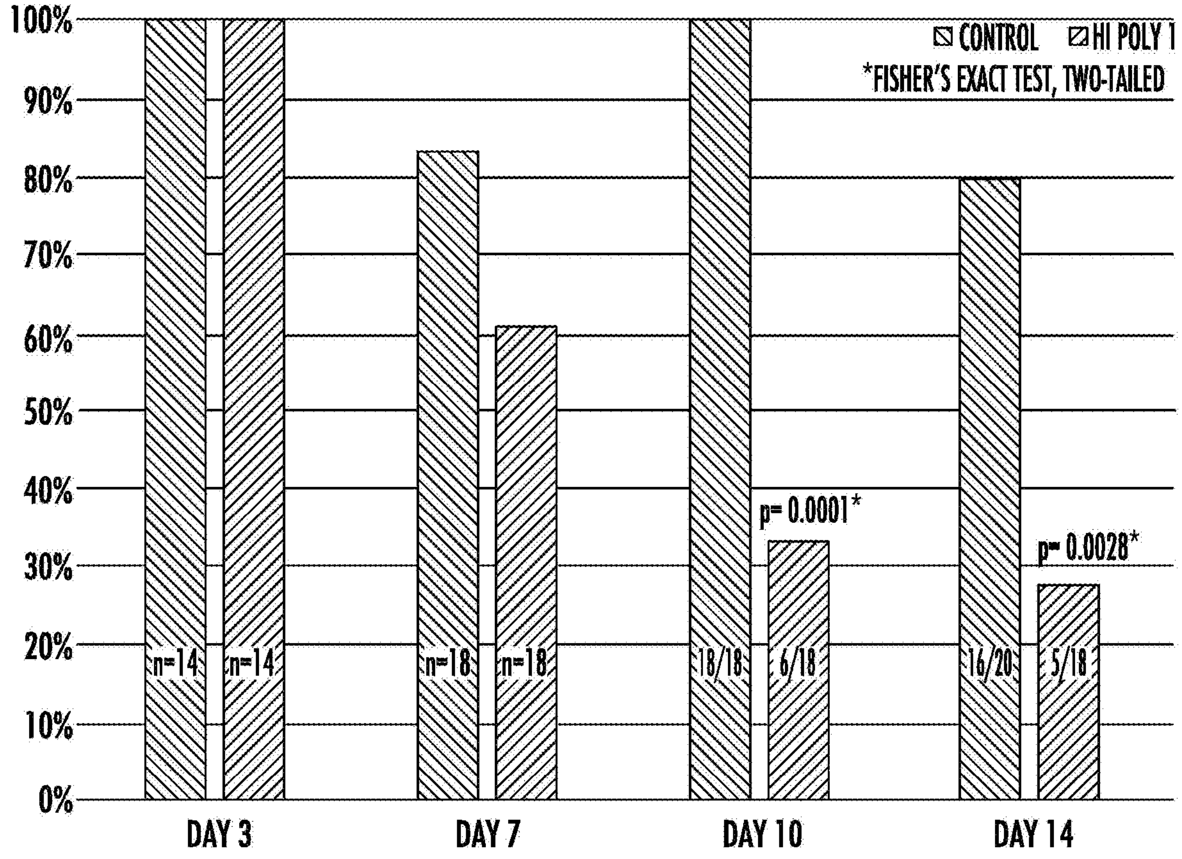
FIG. 15 shows percent of middle ears with detectable effusion (MEE). The number of ears in the control and BVP Hipoly1-immunized chinchilla groups that had detectable middle ear effusions are shown. Ears were determined as dry if no fluids were observed following three separate taps. Sampling was performed on days 3, 7, 10, and 14. Using Fisher's exact test there was a statistically significant difference between control and BVP animals on days 10 and 14 (p=0.0001 and 0.00028 respectively). The number inside the bar refers to the number of positive ears and the total cohort size examined.

In addition to the external examination of OM, epitympanic taps were performed on a subgroup of animals from each cohort. At the point of sampling, each ear was graded as wet with an effusion or dry without an effusion. Dry ears were sampled three separate times to ensure no effusion was present. Effusions were quantitatively cultured to determine the bacterial titer. FIG. 15 shows the percent of dry ears at each time point. On day 3, effusions were present in all ears examined. On day 7 there was a trending difference between the vaccine-treated and the control group. On days 10 and 14 the difference between these two groups was highly significant (p=0.001 and 0.0028 respectively) with over 70% of the vaccine infected ears showing clearance of middle ear fluid.

Figure 16:
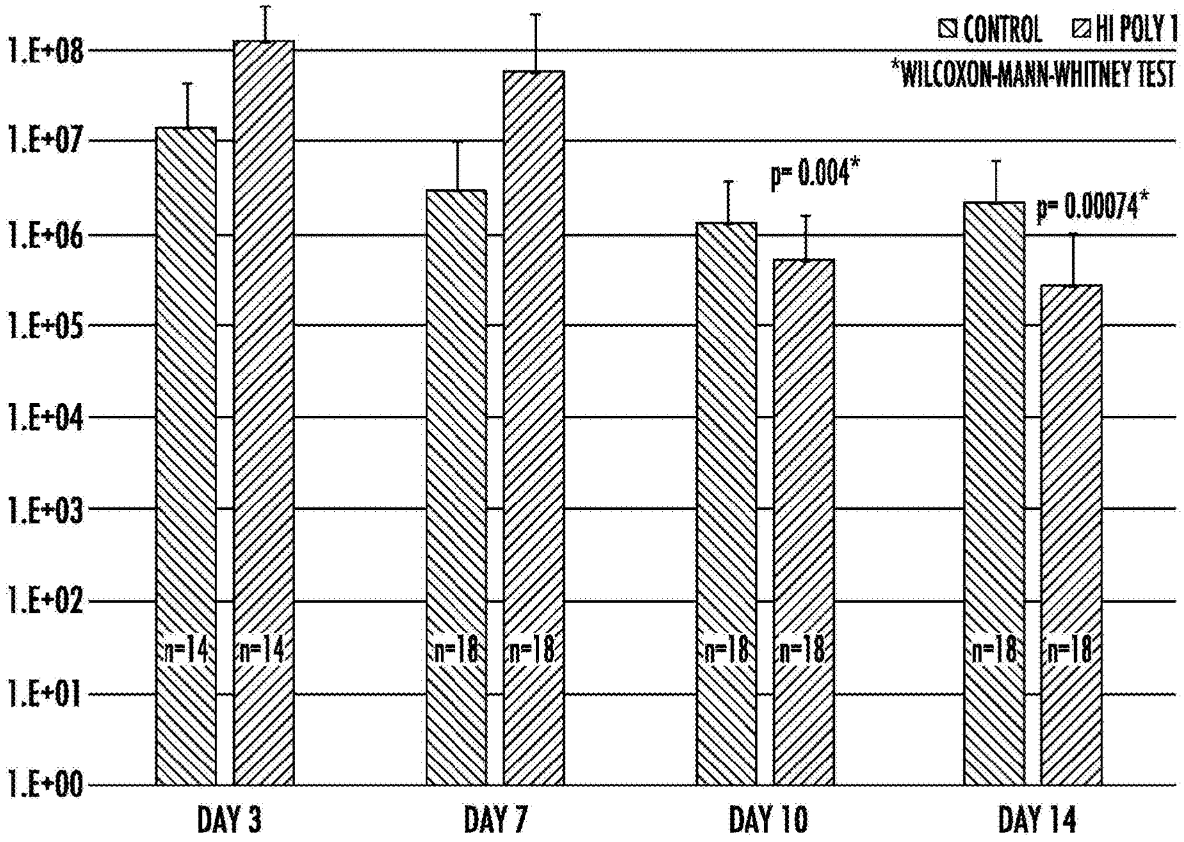
FIG. 16 depicts bacterial titer in middle ear effusions (MEE). The bacterial titers (cfu/ml) for control animals (blue) and animals immunized with the BVP Hi Poly 1 are shown. Data from animals with no detectable middle ear fluid were imputed as 0 cfu/ml. The difference between the control and the Hi Poly 1 groups were significant on days 10 and 14 (p=0.004 and 0.00074, respectively; Wilcoxon-Mann-Whitney test). The number inside the bar is the total number of animals in each group.

FIG. 16 shows the average CFU/ml for MEE. On day 3, the bacterial density in MEE was similar between the vaccine and control groups. However, as the vaccine group cleared the MEE, the bacterial density in the middle ears of the vaccine group was significantly less (p=0.001 and 0.0028 on days 10 and 14 respectively). The MEE bacterial density in the control animals rose over the first few days of infection and averaged $10^6$ cfu/ml over the remainder of the experiment consistent with previous experiments using this model. Most ears of the Hi Poly 1 immunized group cleared the effusion over the 14-day period; however, the bacterial density in the few remaining MEE was not statistically different from MEE in the control group, i.e. approximately $10^6$ cfu/ml.

Discussion

Despite the persistence and high prevalence of significant mucosal and invasive infections due to NTHi, no highly effective, commercially available vaccine is available. The immunoprotection of several virulence factors, including major and minor outer membrane proteins, adhesins, and lipooligosaccharide has been investigated. Peptide motifs of the pilins were shown to protect. However, protection was limited to the homologous strain, presumably a result of known sequence heterogeneity of the pilin proteins. Additionally an 11-valent pneumococcal vaccine using the Hi protein D as a carrier molecule afforded 35% protection against NTHi OM in a clinical trial.

Using bioinformatics and protein structural analysis, we have previously identified peptide regions of multiple NTHi surface proteins that are present throughout the species, are sequence conserved, and individually mediate passive protection in an infant rat model. The process of identifying the protective peptides is unbiased in relation to biological function, and it is noteworthy that the peptides derive from proteins with a variety of functions and structures. Peptides incorporated into Hi Poly 1 are from β-barrels and lipoproteins. HxuC is a TonB-dependent, outer membrane spanning, gated porin involved in the uptake of heme. Protein BamA is also a β-barrel and is involved in the assembly and incorporation of other proteins into the OM. The lipoprotein LptE is an accessory protein to the barrel-structured LptD and contributes to incorporating lipooligosaccharide into the OM. NucA is a membrane anchored, surface exposed 5'-nucleotidase and Hel (lipoprotein e:P4) is a phosphomonoesterase involved in both heme and NAD acquisition. The biological function of the Novel Lipoprotein NlpI has yet to be determined. Thus, the 28 kDa polypeptide Hi Poly 1 targets multiple biologically diverse proteins.

Previous efforts using peptides as bacterial vaccines have been unsuccessful. Lack of immunogenicity due to small size, inability to identify surface exposure, and lack of sequence conservation have limited the utility of peptides in bacterial vaccines. The central hypothesis of the current study is that these obstacles can be overcome with the methodology of BVP using NTHi protective peptides delivered in sequence. Hi Poly 1 proved to be immunogenic, with a $Log_2$ titer of 17.04 (1/134,756). Hi Poly 1 also induced peptide-specific antibodies ranging from a $Log_2$ titer of 4.03 (1/16.3) to 15.27 (1/39,500). Overall, Hi Poly 1 was immunogenic, similar to other proteins used as vaccines. Detailed comparison with current vaccines is difficult since the immunogenicity and protective effectiveness of specific protein regions is not usually characterized. In addition to immunogenicity, we demonstrated that antibodies targeting Hi Poly 1 were protective against two distinct NTHi isolates in two separate models of infection.

Vaccine adjuvants are important determinants of immunogenicity. We used alum as the adjuvant for the current investigations to mimic childhood vaccines. It is likely that the immunogenicity and the immunogenic profile of Hi Poly 1 could be further improved with the expanding list of commercially available adjuvants, for example ASO1 used in the new Shingrix vaccine. Therefore, it is possible that newly developed adjuvants may improve the immunogenicity and immune profile of future BVPs. We have focused on antibodies as a measure of protection in OM since previous studies, including effectiveness by passive protection, have demonstrated that protection against OM is predominantly mediated by serum antibodies. However, alternative immune pathways may be required to protect against other bacteria, e.g. Pertussis.

Bacterial vaccines have historically utilized 1) whole cells, such as Pertussis vaccines prior to the 1990's, 2) protein virulence factors such as tetanus toxin and fimbriae, or 3) surface carbohydrate either alone or conjugated to carrier proteins to improve immunogenicity. More recently, a systematic mining of genomic data by reverse vaccinology has yielded protective lipoproteins useful in meningococcus vaccines. These approaches have been highly successful in controlling prevalent infections. They also have certain limitations. For example, the capsular vaccines target the members of the species with specific capsular types and leave nonencapsulated strains (in the case of *H. influenzae*) or strains with different capsular types (in the case of *Streptococcus pneumoniae*) to cause residual disease. In the case of Pertussis, the current vaccines have 3-5 proteins, one of which is pertactin; strains that do not produce pertactin have recently emerged and may contribute to reduced vaccine effectiveness. These limitations are reduced in a BVP approach since the targets are the immune accessible protein regions and multiple protein regions are efficiently delivered.

Others have used multiple peptides from sequence variable regions of protective proteins to overcome sequence heterogeneity. However, there are significant advantages to BVPs that target sequence conserved regions of multiple proteins. The presence across the species of sequence-conserved regions of surface exposed proteins suggests that these regions may be required for protein function; thus, antibody inhibition of protein function may enhance the vaccine's effectiveness, similar to interference with virulence factors like toxins. Effective targeting of multiple sites reduces the opportunity for genetic escape since multiple simultaneous mutations would be required to avoid exposure. Finally, targeting multiple different protein targets in a BVP offers a highly cost-effective manufacturing approach.

One current limitation to BVPs is the lack of basic tools to identify specific protein regions available for immune attack. This limitation is complicated by the complexity and regulated expression of bacterial surface structures. For example, HxuC is iron/heme regulated and was detected in the current study by extensive animal screening. Also, the specific immune mechanisms required for killing different bacterial species could influence the selection of peptides and is not well investigated. Similarly, methods to identify and distinguish the protective roles of linear and secondary epitopes are not well characterized. Investigations in these areas will be critical for further advancement of BVP.

Polypeptides have been designed in silico to perform a variety of functions, e.g. enzymatic and therapeutic polypeptides. We propose that BVPs be specifically designed to induce protective immunity targeting multiple proteins on the surface of bacteria. Our data focus on the relevant human pathogen NTHi. However, because understanding biological function is not a critical step in the BVP methodology, the approach can be applied directly to other bacterial species. For example, we have evidence that a BVP is effective in a preclinical model of Pertussis (data not shown).

Conclusion. Hi Poly 1, a Bacterial Vaccine Polypeptide, was designed as a multi-targeted polypeptide comprised of sequence-conserved peptides from surface exposed proteins present in all strains of *Haemophilus influenzae*. Hi Poly 1 was immunogenic in chinchillas, and antibodies were induced against each of the component peptides. Post-immunization chinchilla antisera reduced NTHi R2866 bacteremia in the infant rat model compared to PBS or pre-immune sera. Similarly, in the well-established chinchilla model of nontypable *Haemophilus influenzae* (NTHi) otitis media, the vaccine group cleared infection with NTHi strain 86-028 significantly more quickly than the control group. The data support further investigation of Hi Poly 1 as an NTHi vaccine and provide a model for development of Bacterial Vaccine Polypeptides for other pathogens.

Any of the peptide compositions described above or otherwise contemplated herein may further comprise a pharmaceutically acceptable carrier, vehicle, diluent, and/or adjuvant.

Certain embodiments of the present disclosure are directed to a peptide composition comprising at least one fusion heterologous polypeptide (fusion protein) able to induce an antibody response against an infectious organism. The fusion polypeptide may include one, two, three, four, five, six, seven, eight, nine, ten, or more, different peptides linked in series, wherein each of the one or more peptides is from 10 to 60 amino acids in length.

In certain other embodiments, the present disclosure is directed to a peptide composition able to induce an antibody response against a *B. pertussis*, wherein the peptide composition is a carrier molecule composition comprising at least one peptide coupled to a carrier molecule.

Any of the carrier molecule compositions described above or otherwise contemplated herein may be present in a composition that also includes a pharmaceutically acceptable carrier, vehicle, diluent, and/or adjuvant.

In certain embodiments, the present disclosure is directed to a method of inducing in a subject an active or passive immunogenic response against an infectious organism. The method includes the step of administering to a subject an immunogenically-effective amount of any of the peptide compositions, fusion polypeptides, and/or carrier molecule compositions as described above or otherwise contemplated herein.

In certain embodiments, the present disclosure is directed to a method of providing an active or passive immune protection in a subject against *B. pertussis*. The method includes the step of administering to a subject an effective amount of an antibody composition raised against any of the immunogenic peptide compositions, fusion polypeptides, and/or carrier molecule compositions as described above or otherwise contemplated herein.

Moreover, in some embodiments, the DNA encoding heterologous polypeptides can be used as vaccine compositions, whether delivered directly or via a viral vector.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in subsequent patent applications.

REFERENCES

The following references, to the extent that they provide exemplary procedural or other details supplementary to those set forth herein, are specifically incorporated herein by reference.

Gabutti, G., Azzari, C, Bonanni, P, Prato, R, Tozzi, A, Zanetti, A., and Zuccotti, G. Pertussis: *Current perspectives on epidemiology and prevention Human Vaccines* & *Immunother* 11:108-117, 2015

Plotkin S A. 2014. Pertussis: Pertussis control strategies and the options for improving current vaccines. Expert Rev Vaccines 13: 1071-1072.

Burns D L, Meade B D, Messionnier N E. Pertussis Resurgence: Perspectives From the Working Group Meeting on Pertussis on the Causes, Possible Paths Forward, and (Giaps in Our Knowledge. J Infect Dis 2014; 209:S32-S5;

CDC, Pertussis (Whooping Cough) cdc.gov/pertussis/surv-reporting/cases-by-year.html Marieke J. Bart et al., Global Population Structure and Evolution of *Bordetella pertussis* and Their Relationship with Vaccination. mBio. 2014 March-April; 5(2): e01074-14.

Schmidtke A J, Boney K O, Martin S W, Skoff T H, Tondella M L, Tatti K M. Population diversity among *Bordetella pertussis* isolates, United States, 1935-2009. Emerg Infect Dis. 2012 August [Cited 15 Oct. 2012].

CDC, Pregnancy and Whooping Cough, cdc.gov/pertussis/pregnant/mom/get-vaccinated.html

---

What is claimed is:

1. A method of making a *B. pertussis* vaccine composition comprising expressing and purifying a polypeptide consisting of eight peptides in order as set forth in SEQ ID NOS. 11-18.

2. A method of inducing a protective immune response in a subject, comprising administering to the subject an amount of the polypeptide according to claim 1 that is effective in stimulating a protective immune response against *B. pertussis.*

3. The method of claim 2, wherein said polypeptide is further linked to a carrier molecule to form a carrier molecule composition.

4. The method of claim 2, wherein the polypeptide further comprises a pharmaceutically acceptable carrier, vehicle, diluent, and/or adjuvant.

* * * * *